US009156906B2

(12) United States Patent
Franco

(10) Patent No.: US 9,156,906 B2
(45) Date of Patent: Oct. 13, 2015

(54) GLYCOPEPTIDES AND METHODS OF MAKING AND USING THEM

(75) Inventor: Alessandra Franco, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 844 days.

(21) Appl. No.: 12/918,155

(22) PCT Filed: Feb. 26, 2009

(86) PCT No.: PCT/US2009/035340
§ 371 (c)(1),
(2), (4) Date: Nov. 10, 2010

(87) PCT Pub. No.: WO2009/108807
PCT Pub. Date: Sep. 3, 2009

(65) Prior Publication Data
US 2011/0045046 A1    Feb. 24, 2011

Related U.S. Application Data

(60) Provisional application No. 61/031,387, filed on Feb. 26, 2008, provisional application No. 61/038,832, filed on Mar. 24, 2008.

(51) Int. Cl.
| | | |
|---|---|---|
| *C07K 9/00* | (2006.01) | |
| *C07K 7/00* | (2006.01) | |
| *A61K 38/04* | (2006.01) | |
| *C07K 16/18* | (2006.01) | |
| *A61K 38/06* | (2006.01) | |
| *A61K 39/00* | (2006.01) | |
| *C07K 14/47* | (2006.01) | |

(52) U.S. Cl.
CPC ............. *C07K 16/18* (2013.01); *A61K 38/06* (2013.01); *A61K 39/0007* (2013.01); *C07K 9/001* (2013.01); *C07K 14/4727* (2013.01); *A61K 2039/505* (2013.01); *A61K 2039/55566* (2013.01)

(58) Field of Classification Search
CPC ............. C07K 9/00; C07K 7/00; A61K 38/04
USPC ............. 424/450, 185.1, 422; 514/21.4, 21.5, 514/21.6, 21.7, 19.3; 530/322
See application file for complete search history.

(56) References Cited

U.S. PATENT DOCUMENTS

| 7,342,094 B1* | 3/2008 | Karsten et al. ................ 530/326 |
| 2003/0064916 A1 | 4/2003 | Sherman |
| 2004/0132640 A1* | 7/2004 | DeFrees et al. .................. 514/8 |
| 2006/0094649 A1 | 5/2006 | Keogh et al. |
| 2006/0142546 A1* | 6/2006 | Hanisch ........................ 530/322 |
| 2007/0184022 A1 | 8/2007 | Wang et al. |
| 2007/0237785 A1 | 10/2007 | Bay et al. |

FOREIGN PATENT DOCUMENTS

| EP | 1801118 A1 | 6/2007 |
| WO | 9934824 A2 | 7/1999 |
| WO | 0052046 A1 | 9/2000 |
| WO | 0118035 A2 | 3/2001 |
| WO | WO03/089574 | * 10/2003 |

OTHER PUBLICATIONS

Celis (J of Clinical Investigation, 2002, 110:1765-1768).*
Bartell, Written Opinion issued in PCT/US2009/035340, Australian Patent Office, May 6, 2009.
Dziadek et al., A Fully Synthetic Vaccine Consisting of a Tumor-Associated Glycopeptide Antigen and a T-Cell Epitope for the Induction of a Highly Specific Humoral Immune Response, Angew. Chem. Int. Ed. 2005, 44, 7630-7635.
Franco, et al., "Epitope affinity for MHC class I determines helper requirement for CTL priming", Nature Immunology, Aug. 2000, vol. 1, No. 2, pp. 145-150.
Franco, CTL-Based Cancer Preventive/Therapeutic Vaccines for Carcinomas: Role of Tumour-Associated Carbohydrate Antigens, Scandinavian Journal of Immunology, 61, 2005, 391-397.
Franco, "Glycoconjugates As Vaccines for Cancer Immunotherapy: Clinical Trials and Future Directions," Anti-Cancer Agents in Medicinal Chemistry, 2008, vol. 8, No. 1, pp. 1-6.
Gathuru et al., "Identification of DHBcAg as a potent carrier protein comparable to KLH for augmenting MUC1 antigenicity," Vaccine, 23 (2005), 4727-4733.
George et al., "Chemoenzymatic Synthesis of Sialylated Glycopeptides Derived from Mucins and T-Cell Stimulating Peptides," Journal of the American Chemical Society, vol. 123, No. 45, Nov. 14, 2001, pp. 11117-11125.
Geyer et al., "Characterization of keyhole limpet hemocyanin (KLH) glycans sharing a carbohydrate epitope with Schistosoma mansoni glycoconjugates," Micron, 35 (2004), pp. 105-106.
Gilewski et al., "Immunization of High-Risk Breast Cancer Patients with Clustered sTn-KLH Conjugate plus the Immunologic Adjuvant QS-21," Clin. Cancer Res. 2007, 13(10), May 15, 2007, pp. 2977-2985.
Ingale, et al., "Robust immune responses elicited by a fully synthetic three-component vaccine," Nature Chemical Biology, vol. 3, No. 10, Oct. 2007, pp. 663-667.
Kagan, et al., "Comparison of antigen constructs and carrier molecules for augmenting the immunogenicity of the monosaccharide epithelial cancer antigen Tn," Cancer Immunol. Immunother, (2005) 54:424-430.
Novellino et al., A listing of human tumor antigens recognized by T cells: Mar. 2004 Update, Cancer Immunol. Immunother. (2005) 54:187-207.

(Continued)

*Primary Examiner* — Yan Xiao
(74) *Attorney, Agent, or Firm* — Gregory P. Einhorn; Greer, Burns & Crain, Ltd.

(57) ABSTRACT

In one embodiment, the invention provides glycopeptides (or carbohydrate-peptide conjugates) comprising TACAs that direct against (e.g., bind specifically to) cytotoxic T lymphocytes (CTLs) or helper T cells for, e.g., CTL- or T-helper-based immunotherapy of carcinomas, and methods for making and using the glycopeptides of the invention. In one embodiment, the invention provides novel glycopeptides comprising tumor-derived carbohydrate or tumor-derived epitopes that specifically bind to major histocompatibility (MHC) class I molecules on cytotoxic T lymphocytes (CTLs) or MHC molecules on helper T cells, and methods for using same, e.g., as a vaccine, including a pan-cancer vaccine.

31 Claims, 7 Drawing Sheets

(56) References Cited

OTHER PUBLICATIONS

Slovin et al., "Thomsen-Friendenrich (TF) antigen as a target for prostate cancer vaccine: clinical trial results with TF cluster (c)-KLH plus QS21 conjugate vaccine in patients with biochemically relapsed prostate cancer," Cancer Immunol. Immunother. (2005) 54:694-702.

Slovin et al., "A bivalent conjugate vaccine in the treatment of biochemically relapsed prostate cancer: a study of glycosylated MUC-2-KLH and Globo H-KLH conjugate vaccines given with the new semi-synthetic saponin immunological adjuvant GPI-0100 or QS-21," Vaccine 23 (2005) 3114-3122.

Svarovsky et al., "Synthesis of gold nanoparticles bearing the Thomsen-Friedenreich disaccharide: a new multivalent presentation of an important tumor antigen," Tetrahedron: Asymmetry 16 (2005) 587-598.

Xu et al., "Designer Glycopeptides for Cytotoxic T Cell-Based Elimination of Carcinomas," The Journal of Experimental Medicine, vol. 199, No. 5, Mar. 1, 2004, pp. 707-716.

Xu et al., "Tumor-associated carbohydrate antigens: A possible avenue for cancer prevention," Immunology and Cell Biology (2005) 83, 440-448.

* cited by examiner

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 1

Phe Leu Pro Asp Thr Arg Phe Tyr Val
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 2

Phe Leu Phe Pro Asp Thr Arg Ala Val
 1               5

<210> SEQ ID NO 3
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 3

Phe Leu Phe Pro Asp Thr Arg Tyr Val
 1               5

<210> SEQ ID NO 4
```

```
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 4

Ala Leu Gly Ser Thr Ala Pro Pro Val
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 5

Ser Ala Phe Pro Thr Thr Ile Asn Phe
 1               5

<210> SEQ ID NO 6
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 6

Ser Ala Phe Pro Thr Thr Ile Asn Phe
 1               5

<210> SEQ ID NO 7
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(11)
<223> OTHER INFORMATION: peptide

<400> SEQUENCE: 7

Arg Glu Pro Val Thr Thr Lys Ala Glu Met Leu
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 8
```

```
Glu Ala Asp Pro Thr Gly His Ser Tyr
1               5
```

<210> SEQ ID NO 9
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(10)
<223> OTHER INFORMATION: peptide

<400> SEQUENCE: 9

```
Arg Glu Pro Val Thr Lys Ala Glu Met Leu
1               5                   10
```

<210> SEQ ID NO 10
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 10

```
Met Val Lys Ile Ser Gly Gly Pro Arg
1               5
```

<210> SEQ ID NO 11
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 11

```
Lys Ile Phe Gly Ser Leu Ala Phe Leu
1               5
```

<210> SEQ ID NO 12
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 12

```
Ile Leu His Asn Gly Ala Tyr Ser Leu
1               5
```

<210> SEQ ID NO 13
<211> LENGTH: 9
<212> TYPE: PRT
<213> ORGANISM: Artificial Sequence
<220> FEATURE:
<223> OTHER INFORMATION: synthetic construct

```
<220> FEATURE:
<221> NAME/KEY: PEPTIDE
<222> LOCATION: (1)...(9)
<223> OTHER INFORMATION: peptide

<400> SEQUENCE: 13

Cys Leu Thr Ser Thr Val Gln Leu Val
 1               5

<210> SEQ ID NO 14
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(11)
<223> OTHER INFORMATION: peptide

<400> SEQUENCE: 14

Leu Leu Pro Glu Asn Asn Val Leu Ser Pro Leu
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(11)
<223> OTHER INFORMATION: peptide

<400> SEQUENCE: 15

Leu Leu Pro Glu Asn Asn Val Leu Ser Pro Val
 1               5                  10

<210> SEQ ID NO 16
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 16

Leu Leu Gly Arg Asn Ser Phe Glu Val
 1               5

<210> SEQ ID NO 17
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 17

Leu Leu Gly Arg Asn Ser Phe Glu Val
 1               5
```

```
<210> SEQ ID NO 18
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(10)
<223> OTHER INFORMATION: A2 binding peptide

<400> SEQUENCE: 18

Phe Leu Pro Ser Asp Phe Phe Pro Ser Val
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: A2 binding peptide

<400> SEQUENCE: 19

Gly Leu Tyr Ser Ser Thr Val Pro Val
 1               5

<210> SEQ ID NO 20
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: A2 binding peptide

<400> SEQUENCE: 20

Phe Leu Leu Ser Leu Gly Ile His Leu
 1               5

<210> SEQ ID NO 21
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: A2 binding peptide

<400> SEQUENCE: 21

Thr Leu Thr Ser Cys Asn Thr Ser Val
 1               5

<210> SEQ ID NO 22
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: A2 binding peptide
```

```
<400> SEQUENCE: 22

Ala Leu Ala Ser Ala Ala Ala Ala Val
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: MUC1 signal sequence

<400> SEQUENCE: 23

Leu Leu Leu Leu Thr Val Leu Thr Val
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: designer/MUC1-core

<400> SEQUENCE: 24

Phe Leu Pro Asp Thr Arg Phe Ala Val
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: designer/MUC1-core

<400> SEQUENCE: 25

Phe Leu Pro Asp Thr Arg Phe Tyr Val
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: designer/MUC1-core

<400> SEQUENCE: 26

Phe Leu Phe Pro Asp Thr Arg Ala Val
1               5

<210> SEQ ID NO 27
<211> LENGTH: 9
<212> TYPE: PRT
<213> ORGANISM: Artificial Sequence
<220> FEATURE:
```

```
<223> OTHER INFORMATION: synthetic construct
<220> FEATURE:
<221> NAME/KEY: PEPTIDE
<222> LOCATION: (1)...(9)
<223> OTHER INFORMATION: designer/MUC1-core

<400> SEQUENCE: 27

Phe Leu Phe Pro Asp Thr Arg Tyr Val
 1               5

<210> SEQ ID NO 28
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: peptide

<400> SEQUENCE: 28

Ala Ile Ile Ala Ser Phe Ala Ala Leu
 1               5

<210> SEQ ID NO 29
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(20)
<223> OTHER INFORMATION: peptide

<400> SEQUENCE: 29

His Gly Val Thr Ser Ala Pro Asp Thr Arg Pro Ala Pro Gly Ser Thr
 1               5                  10                  15

Ala Pro Pro Ala
            20
```

US 9,156,906 B2

GLYCOPEPTIDES AND METHODS OF MAKING AND USING THEM

This application is a national phase patent utility filing under 35 USC §371, for international application no. PCT/US2009/035340, filed on Feb. 26, 2009, which claims the benefit of priority to U.S. utility provisional patent application Ser. No. 61/031,387, filed Feb. 26, 2008; and U.S. Ser. No. 61/038,832, filed Mar. 24, 2008. The aforementioned applications are explicitly incorporated herein by reference in their entirety and for all purposes.

STATEMENT AS TO FEDERALLY SPONSORED RESEARCH

This invention was made with government support under grant No. DAMD17-02-1-0436 awarded by the U.S. Department of Defense. The government has certain rights in the invention.

FIELD OF THE INVENTION

This invention generally relates to immunology, tumor biology and medicine. In one embodiment, the invention provides cancer immunotherapies and pan-cancer vaccines. In alternative embodiments, vaccines of the invention are used to generate cancer antigen specific cell-based and/or humoral (antibody) immune responses, wherein in one embodiment the cancer antigen is a Tumor Associated Carbohydrate Antigen (TACA). In one embodiment, the invention provides glycopeptides (or carbohydrate-peptide conjugates) comprising TACAs that direct against (e.g., bind specifically to) cytotoxic T lymphocytes (CTLs) or helper T cells for, e.g., CTL- or T-helper-based immunotherapy of cancers such as carcinomas, and methods for making and using the glycopeptides of the invention. In one embodiment, the invention provides novel glycopeptides comprising tumor-derived carbohydrate or tumor-derived epitopes that specifically bind to major histocompatibility (MHC) class I molecules on cytotoxic T lymphocytes (CTLs) or MHC molecules on helper T cells, and methods for using same, e.g., as a vaccine.

BACKGROUND OF INVENTION

Peptides derived from tumor epitopes are known to generate peptide-specific cytotoxic T cell responses. Tumor-associated carbohydrate antigens linked to immunogenic carrier proteins or in multimeric forms are used for antibody production, e.g., targeting B cell responses. The concept of a pan-cancer vaccine has been attractive for preventive use in normal healthy individuals and use post surgery or post chemo/radiation to minimize metastasis or limit further metastasis. Tumor Associated Carbohydrate Antigens (TACA) antigens as Thomsen-Friedenreich (TF) (Gal beta (β) 1-3GalNAc alpha (α) 1-R) and Tn (TF precursor, GalNAc alpha (α) 1-R) antigens have been used in a variety of formulation for the generation of specific antibodies in cancer patients. Traditional approaches have not been very successful in part because of the difficulties of manufacturing the requisite peptide derivatives and isolating the adjuvant proteins.

TF and Tn are expressed by mucins encoded in humans by the MUC1 gene. TF and Tn are precursors of the MN blood group substance expressed on glycophorin, which is also expressed on MUC1 found on tumor cells.

The productive development of memory CD8+ cytotoxic T cells (CTL) against tumors primarily depends on the strength of the antigenic stimuli, a consequence of the binding affinity of tumor antigens to class I molecules of the major histocompatibility complex (MHC), and the affinity of T cell receptors (TcRs) to MHC/peptide complexes. The homing and route of immunization also play an important role in determining the size of the initial CTL burst, depending on the participation of other immune cells that provide chemokines/lymphokines and co-stimulatory stimuli. Two big limitations in designing T cell-based immunotherapy against tumors are the characterization of immunogenic tumor epitopes and the frequent "self" nature of tumor antigens that leads to immunological tolerance.

SUMMARY OF THE INVENTION

The invention provides compositions and methods comprising glycopeptides (or carbohydrate-peptide conjugates) for use as pharmaceuticals, e.g., as vaccines. In one embodiment, the invention provides cancer immunotherapies and pan-cancer vaccines.

In alternative embodiments, the invention provides isolated glycopeptide (glycoconjugate) comprising
(a) at least one carbohydrate moiety conjugated (linked) to:
(i) a tumor-associated antigen (TAA)-derived peptide, or
(ii) a peptide (or polypeptide) comprising or consisting of at least one tumor epitope;
wherein the peptide is between about 8 to 14 (i.e., 8, 9, 10, 11, 12, 13 or 14), or about 6 to 20 (i.e., 6, 7, 8, 9, 10, 11, 12, 13, 14, 15, 16, 17, 18, 19 or 20), or about 5 to 30 (i.e., 5, 6, 7, 8, 9, 10, 11, 12, 13, 14, 15, 16, 17, 18, 19, 20, 21, 22, 23, 24, 25, 26, 27, 28, 29 or 30) or more amino acid residues in length,
and the at least one carbohydrate moiety is conjugated (linked) to the peptide or at least one tumor epitope at an amino acid residue central to (within) the peptide or tumor epitope;
(b) the glycopeptide (glycoconjugate) of (a), wherein the peptide or tumor epitope is a carcinoma-derived or a carcinoma-associated peptide or peptide amino acid sequence;
(c) the glycopeptide (glycoconjugate) of (a), wherein the peptide (or polypeptide) comprises one or more non-naturally occurring residues, or one or more peptidomimetic residues;
(d) the glycopeptide (glycoconjugate) of any of (a) to (c), wherein the peptide (or polypeptide) is between about 8 to 14, or about 6 to 20, or about 5 to 30 or more, amino acid residues in length;
(e) the glycopeptide (glycoconjugate) of any of (a) to (e), wherein the at least one tumor epitope consists of three, four, five or six or more amino acid residues;
(f) at least one carbohydrate moiety conjugated (linked) to a peptide (or polypeptide),
wherein the peptide comprises or consists of:

| | |
|---|---|
| FLPDTRFYV, | (SEQ ID NO: 1) |
| FLFPDTRAV, or | (SEQ ID NO: 2) |
| FLFPDTRYV; | (SEQ ID NO: 3) |

(g) the carbohydrate moiety of any of (a) to (f), wherein the at least one carbohydrate moiety is a tumor-associated carbohydrate antigen (TACA) or a tumor-derived carbohydrate; or
(h) at least one tumor-associated carbohydrate antigen (TACA) or a tumor-derived carbohydrate conjugated (linked) to a peptide (or polypeptide), wherein the peptide comprises or consists of:

| | |
|---|---|
| ALGSTAPPV, | (SEQ ID NO: 4) |
| SAFPTTINF, | (SEQ ID NO: 5) |
| SAFPTTINF, | (SEQ ID NO: 6) |
| REPVTTKAEML, | (SEQ ID NO: 7) |
| EADPTGHSY, | (SEQ ID NO: 8) |
| REPVTKAEML, | (SEQ ID NO: 9) |
| MVKISGGPR, | (SEQ ID NO: 10) |
| KIFGSLAFL, | (SEQ ID NO: 11) |
| ILHNGAYSL, | (SEQ ID NO: 12) |
| CLTSTVQLV, | (SEQ ID NO: 13) |
| LLPENNVLSPL, | (SEQ ID NO: 14) |
| LLPENNVLSPV, | (SEQ ID NO: 15) |
| LLGRNSFEV, | (SEQ ID NO: 16) |
| LLGRNSFEV, | (SEQ ID NO: 17) |
| or | |
| HGVTSAPDTRPAPGSTAPPA, | (SEQ ID NO: 29) | and the at least one tumor-associated carbohydrate antigen (TACA) or a tumor-derived carbohydrate is conjugated (linked) to the peptide at an amino acid residue central to (within) the peptide.

In one embodiment of the glycopeptide, the at least one carbohydrate moiety is covalently attached to the peptide or tumor epitope, or, the at least one carbohydrate moiety is conjugated (linked) to the peptide:
  (i) at an amino acid residue central to the peptide, or
  (ii) at an amino acid residue that is not an anchor for the major histocompatibility complex (MHC) polypeptide (at an amino acid residue not involved in the peptide's binding to an MHC polypeptide) or an amino acid residue that is not part of the tumor epitope; and/or the carbohydrate moiety is conjugated (linked) to the peptide at:
    (a) for a peptide about 8 to 16 amino acids residues in length, at position 3, 4, 5, 6, 7 and/or 8 of the peptide (where position 1 is the first amino terminal amino acid residue),
    (b) for a peptide about 20 amino acids residues in length, at position 3, 4, 5, 6, 7, 8, 9, 10, 11, 12, 13, 14, 15 or 16 of the peptide (where position 1 is the first amino terminal amino acid residue),
    (c) for a peptide about 30 amino acids residues in length, at position 3, 4, 5, 6, 7, 8, 9, 10, 11, 12, 13, 14, 15, 16, 17, 18, 19, 20, 21, 22, 23, 24, 25, 26, 27 or 28 of the peptide (where position 1 is the first amino terminal amino acid residue), or
    (d) no amino acid residue within two residues of the amino terminal end or carboxy terminal end of the peptide (the carbohydrate moiety is conjugated (linked) to the peptide at least three amino acid residues in from either the amino terminal or carboxy terminal end of the peptide).

In one embodiment of the glycopeptide, the at least one carbohydrate moiety of the glycopeptide (glycoconjugate) is a monosaccharide, a disaccharide, a trisaccharide or a polysaccharide. The at least one carbohydrate moiety of the glycopeptide (glycoconjugate) can be sialated, or all of the carbohydrate moieties of the glycopeptide (glycoconjugate) can be sialated, or none of the carbohydrate moieties of the glycopeptide (glycoconjugate) can be sialated.

In one embodiment of the glycopeptide, the at least one carbohydrate moiety of the glycopeptide (glycoconjugate) comprises or consists of at least one tumor-associated carbohydrate antigen (TACA), or at least one or tumor-derived carbohydrate. The at least one tumor associated carbohydrate or at least one tumor associated carbohydrate antigen (TACA) can be only expressed on one or a subset of tumor or cancer cells and is not expressed on any normal cells.

The carbohydrate moiety can be any combination of carbohydrates, including N-linked and/or O-linked or artificially linked, including e.g., tumor-associated carbohydrate antigen (TACA) and/or non-tumor-derived carbohydrate(s) alone or in combination. For example, in alternative embodiments, the carbohydrate moiety can be any combination of β-D-glucose, β-D-galactose, β-D-mannose, α-L-Fucose, N-Acetylgalactosamine (also called GalNAc, 2-Acetamido-2-deoxy-D-galactopyranose or N-Acetyl-D-galactosamine), N-Acetylglucosamine (N-Acetyl-D-Glucosamine, or GlcNAc, or NAG), or any aminoglycoside or amino hexose sugar, N-Acetylneuraminic acid (Neu5Ac or NANA), sialic acid, Neuraminic acid (5-amino-3,5-dideoxy-D-glycero-D-galacto-non-2-ulosonic acid), or xylose or any pentose sugar.

In alternative embodiments of the glycopeptides of the invention, the glycopeptide (glycoconjugate) comprises or consists of:

| | |
|---|---|
| FLPD(X-T)RFYV, | (FLPDTRFYV is SEQ ID NO: 1) |
| FLFPD(X-T)RAV, | (FLFPDTRAV is SEQ ID NO: 2) |
| FLFPD(X-T)RYV, | (FLFPDTRYV is SEQ ID NO: 3) |
| ALG(X-S)TAPPV, | (ALGSTAPPV is SEQ ID NO: 4) |
| ALGS(X-T)APPV | (ALGSTAPPV is SEQ ID NO: 5) |
| SAFP(X-T)TINF, | (SAFPTTINF is SEQ ID NO: 6) |
| SAFPT(X-T)INF, | (SAFPTTINF is SEQ ID NO: 7) |
| REPV(X-T)TKAEML, | (REPVTTKAEML is SEQ ID NO: 8) |
| EADP(X-T)GHSY, | (EADPTGHSY is SEQ ID NO: 9) |
| REPV(X-T)KAEML, | (REPVTKAEML is SEQ ID NO: 10) |
| MVKI(X-S)GGPR, | (MVKISGGPR is SEQ ID NO: 11) |
| KIFG(X-S)LAFL, | (KIFGSLAFL is SEQ ID NO: 12) |
| ILH(X-N)GAYSL, | (ILHNGAYSL is SEQ ID NO: 13) |
| CLT(X-S)TVQLV, | (CLTSTVQLV is SEQ ID NO: 13) |
| CLTS(X-T)VQLV, | (CLTSTVQLV is SEQ ID NO: 14) |
| LLPE(X-N)NVLSPL, | (LLPENNVLSPL is SEQ ID NO: 15) |
| LLPEN(X-N)VLSPV, | (LLPENNVLSPV is SEQ ID NO: 16) |
| LLGR(X-N)SFEV, | (LLGRNSFEV is SEQ ID NO: 17) |
| LLGRN(X-S)FEV, | (LLGRNSFEV is SEQ ID NO: 18) |
| HGV(X-T)SAPDTRPAPGSTAPPA, | (SEQ ID NO: 29) |
| (HGVTSAPDTRPAPGSTAPPA is SEQ ID NO: 29) | |
| HGVT(X-S)APDTRPAPGSTAPPA, | (SEQ ID NO: 29) |
| HGVTSAPD(X-T)RPAPGSTAPPA, | (SEQ ID NO: 29) |
| HGVTSAPDTRPAPG(X-S)TAPPA, | (SEQ ID NO: 29) |
| or | |
| HGVTSAPDTRPAPGS(X-T)APPA, | (SEQ ID NO: 29) | wherein X comprises or consists of a carbohydrate moiety or a TACA, and/or X comprises or consists of a disaccharide TF (α-Gal-[1->3]-β-GalNAc); a TF precursor, a monomer Tn (α-GalNAc), and/or X comprises or consists of a carbohydrate moiety linked or not linked (conjugated to) one or more sialyl moieties.

In alternative embodiments of the glycopeptides of the invention, the glycopeptide comprises or consists of:

| | |
|---|---|
| FLPD(Tn-T) RFYV, | (SEQ ID NO: 1) |
| FLFPD(Tn-T)RAV, | (SEQ ID NO: 2) |
| FLFPD(Tn-T)RYV, | (SEQ ID NO: 3) |
| ALG(Tn-S)TAPPV, | (SEQ ID NO: 4) |
| ALGS(Tn-T)APPV | (SEQ ID NO: 5) |
| SAFP(Tn-T)TINF, | (SEQ ID NO: 6) |
| SAFPT(Tn-T)INF, | (SEQ ID NO: 7) |
| REPV(Tn-T)TKAEML, | (SEQ ID NO: 8) |
| EADP(Tn-T)GHSY, | (SEQ ID NO: 9) |
| REPV(Tn-T)KAEML, | (SEQ ID NO: 10) |
| MVKI(Tn-S)GGPR, | (SEQ ID NO: 11) |
| KIFG(Tn-S)LAFL, | (SEQ ID NO: 12) |
| ILH(Tn-N)GAYSL, | (SEQ ID NO: 13) |
| CLT(Tn-S)TVQLV, | (SEQ ID NO: 13) |
| CLTS(Tn-T)VQLV, | (SEQ ID NO: 14) |
| LLPE(Tn-N)NVLSPL, | (SEQ ID NO: 15) |
| LLPEN(Tn-N)VLSPV, | (SEQ ID NO: 16) |
| LLGR(Tn-N)SFEV, or | (SEQ ID NO: 17) |
| LLGRN(Tn-S)FEV, | (SEQ ID NO: 18) |
| HGV(Tn-T)SAPDTRPAPGSTAPPA, | (SEQ ID NO: 29) |
| HGVT(Tn-S)APDTRPAPGSTAPPA, | (SEQ ID NO: 29) |
| HGVTSAPD(Tn-T)RPAPGSTAPPA, | (SEQ ID NO: 29) |
| HGVTSAPDTRPAPG(Tn-S)TAPPA, | (SEQ ID NO: 29) |
| HGVTSAPDTRPAPGS(Tn-T)APPA. | (SEQ ID NO: 29) |

In alternative embodiments of the glycopeptides of the invention, the carbohydrate moiety comprises or consists of: the disaccharide TF (α-Gal-[1->3]-β-GalNAc); the TF precursor, the saccharide monomer Tn (α-GalNAc) and/or a mono- or poly-sialyl moiety.

The carbohydrate moiety with (and) its peptide linkage can comprise or consist of:

(a) a disaccharide TF (α-Gal-[1->3]-β-GalNAc-O-), a monomer Tn (α-GalNAc-O-), or a mono- or poly-sialyl-Tn (STn); or (b) a disaccharide TF (α-Gal-[1->3]-β-GalNAc-O-serine); a disaccharide α-Gal-[1->3]-β-GalNAc-O-threonine; a disaccharide α-Gal-[1->3]-β-GalNAc-O-asparagine; saccharide monomer Tn (α-GalNAc-O-serine); a saccharide monomer α-GalNAc-O-threonine; a saccharide monomer α-GalNAc-O-asparagine; or, a mono- or poly-sialyl-Tn (STn).

In alternative embodiments of the glycopeptides of the invention, the peptide comprises or consists of an isolated, synthetic or recombinantly generated peptide or amino acid. The peptide (or polypeptide), or at least one amino acid in the peptide, can comprise or consist of a peptidomimetic or non-natural amino acid residue.

In alternative embodiments, the invention provides compositions comprising one or more (at least one) glycopeptides (glycoconjugates) of the invention.

In alternative embodiments, the invention provides pharmaceutical compositions or formulations comprising one or more (at least one) glycopeptides (glycoconjugates) of the invention and, in one alternative aspect, a pharmaceutically acceptable excipient. The pharmaceutical composition can be formulated as a vaccine, or the pharmaceutical composition can be formulated as a vaccine for administration via a parenteral route comprising or consisting of a subcutaneous, an intravenous (IV), an intradermal, an intramuscular, an intraperitoneal, an intranasal, a transdermal or a buccal route; or the pharmaceutical composition is formulated as a vaccine for oral or topical administration. The pharmaceutical composition can be formulated as a sterile solution for injection, or as a powder or a lyophilized (freeze-dried) composition. The pharmaceutical composition can be formulated as a liquid, an emulsion, a lyophilized powder, a spray, a cream, a lotion, a controlled release formulation, a tablet, a pill, a gel, a patch, in an implant or in a spray; or is formulated as an aqueous or a non-aqueous isotonic sterile injection solution, or an aqueous or a non-aqueous sterile suspension.

In alternative embodiments, the invention provides liposome comprising one or more (at least one) glycopeptides (glycoconjugates) of the invention, and/or the pharmaceutical of the invention or formulation of the invention.

In alternative embodiments, the invention provides nanoparticles comprising one or more (at least one) glycopeptides (glycoconjugates) of the invention; the pharmaceutical or formulation of the invention; or the liposome of the invention.

In alternative embodiments, the invention provides vaccines comprising one or more (at least one) glycopeptides (glycoconjugates) of the invention; the pharmaceutical or formulation of the invention; the liposome of the invention; or the nanoparticle of the invention.

In alternative embodiments, the invention provides uses of one or more (at least one) glycopeptides (glycoconjugates) of the invention; the pharmaceutical or formulation of the invention; the liposome of the invention; or the nanoparticle of the invention, for the manufacture of a medicament or a vaccine.

In alternative embodiments, the invention provides uses of one or more (at least one) glycopeptides (glycoconjugates) of the invention; the pharmaceutical or formulation of the invention; the liposome of the invention; or the nanoparticle of the invention, for the manufacture of a medicament or a vaccine for the treatment, prevent or amelioration of a disease or condition associated with a dysfunctional cell or a cancer or a tumor cell.

In alternative embodiments, the invention provides uses of one or more (at least one) glycopeptides (glycoconjugates) of the invention; the pharmaceutical or formulation of the invention; the liposome of the invention; or the nanoparticle of the invention, for the manufacture of a medicament or vaccine for the treatment, prevent or amelioration of a cancer or a tumor, or for the manufacture of a medicament or vaccine to prevent, decrease the amount of or ameliorate metastasis a cancer or a tumor. In alternative aspects of the use(s), the cancer is of epithelial origin or is a carcinoma, or the cancer is a carcinoma, a lymphoma, Hodgkin's Disease, a chronic or acute leukemia, a lymphocytic lymphoma leukemia, a neoplasm of the central nervous system (CNS), a primary CNS lymphoma, a spinal axis tumor, a brain stem glioma, a pituitary adenoma or a cutaneous or systemic melanoma, or in alternative aspects the carcinoma is a lung cancer, a pancreatic cancer, a skin cancer, a cancer of the head or neck, a uterine cancer, an ovarian cancer, a rectal cancer, a cancer of the anal region, a stomach cancer, a colon cancer, a breast cancer, a carcinoma of the fallopian tubes, a carcinoma of the endometrium, a carcinoma of the cervix, a carcinoma of the vagina, a carcinoma of the vulva, a cancer of the esophagus, a cancer of the small intestine, a cancer of the endocrine system, a cancer of the thyroid gland, a cancer of the parathyroid gland, a cancer of the adrenal gland, a cancer of the urethra, a cancer of the penis, a prostate cancer, a cancer of the bladder, a cancer of the kidney or ureter, a renal cell carcinoma, a carcinoma of the renal pelvis.

In alternative embodiments, the invention provides methods for treating, preventing or ameliorating a disease or condition associated with a dysfunctional cell or a cancer or a tumor cell comprising administering an effective amount of one or more (at least one) glycopeptides (glycoconjugates) of the invention; the pharmaceutical or formulation of the invention; the liposome of the invention; or the nanoparticle of the invention, to an individual in need thereof.

In alternative embodiments, the invention provides methods for treating, preventing or ameliorating a cancer or a tumor, or for preventing, decreasing the amount of or ameliorating metastasis of a cancer or a tumor, comprising administering an effective amount of one or more (at least one) glycopeptides (glycoconjugates) of the invention; the pharmaceutical or formulation of the invention; the liposome of the invention; or the nanoparticle of the invention, to an individual in need thereof. The cancer can be of epithelial origin, or the cancer can be a carcinoma, a lymphoma, Hodgkin's Disease, a chronic or acute leukemia, a lymphocytic lymphoma leukemia, a neoplasm of the central nervous system (CNS), a primary CNS lymphoma, a spinal axis tumor, a brain stem glioma, a pituitary adenoma or a cutaneous or systemic melanoma, or the carcinoma can be a lung cancer, a pancreatic cancer, a skin cancer, a cancer of the head or neck, a uterine cancer, an ovarian cancer, a rectal cancer, a cancer of the anal region, a stomach cancer, a colon cancer, a breast cancer, a carcinoma of the fallopian tubes, a carcinoma of the endometrium, a carcinoma of the cervix, a carcinoma of the vagina, a carcinoma of the vulva, a cancer of the esophagus, a cancer of the small intestine, a cancer of the endocrine system, a cancer of the thyroid gland, a cancer of the parathyroid gland, a cancer of the adrenal gland, a cancer of the urethra, a cancer of the penis, a prostate cancer, a cancer of the bladder, a cancer of the kidney or ureter, a renal cell carcinoma, a carcinoma of the renal pelvis.

In alternative aspects, methods comprise administering an effective amount of one or more (at least one) glycopeptides (glycoconjugates) of the invention; the pharmaceutical or formulation of the invention; the liposome of the invention; or the nanoparticle of the invention, is or are administered as a vaccine. The vaccine can be administered intradermally as a sterile formulation, or as an inhaled powder, or, the vaccine can be administered as a controlled release formulation, a tablet, a pill, a gel, a patch, in an implant or in a spray.

In alternative aspects, the vaccine can be administered with an adjuvant, e.g., the adjuvant can comprise or consist of incomplete Freund's adjuvant (IFA) or MONTANIDE ISA 51®; alum; aluminum phosphate; aluminum hydroxide; squalene; complete Freund's adjuvant (CFA), or levamisole; QS-21™, or STIMULON® (Antigenics, Lexington, Mass.); or muramyl dipeptide (MDP) or derivatives thereof; monophosphoryl lipid (MPL) or derivatives thereof; or monophosphoryl lipid A (MPLA) or derivatives thereof; or MF59™ or FLUAD® (Novartis, Basel, Switzerland); or as described in U.S. Pat. No. 7,182,962; or a glycosylceramide as described e.g. in U.S. Pat. No. 7,488,491; triacyl lipid A or derivatives thereof or OM-174™ (OM Pharma, Geneva, Switzerland); or SB-AS2™, or an oil in water emulsion comprising monophosphoryl lipid A (MPLA) and QS-21™; or SYNTEX™ adjuvant formulation (SAF) (Laboratorios Syntex SA, Mexico City Mexico), or an adjuvant comprising a muramyl dipeptide derivative (threonyl-MDP) in an oil-in-water (o/w) emulsion vehicle; or pluronic L121 or poloxamer 401; or a mucosal adjuvant comprising a detoxified mutant A subunit of a cholera toxin (CT) or an E. coli heat labile toxin (LT1 or LT2) as described in U.S. Pat. No. 7,485,304 (Novartis Vaccines and Diagnostics SRL); or an adjuvant as described in U.S. Pat. No. 7,357,936 (SmithKline Beecham Biologicals, SA); or any combination thereof.

In alternative aspects, the vaccine is administered with a non-specific immuno-stimulator, e.g., the non-specific immuno-stimulator can comprise or consist of a granulocyte-macrophage colony-stimulating factor polypeptide; or sargramostim, or LEUKINE™ (Bayer, Leverkusen, Germany).

In alternative embodiments of the methods, an effective amount of one or more (at least one) glycopeptides (glycoconjugates) of the invention; the pharmaceutical or formulation of the invention; the liposome of the invention; or the nanoparticle of the invention, is an amount sufficient to generate (elicit) an antigen-specific cytotoxic lymphocyte (CTL) response and/or an antigen-specific helper T cell response, and/or a CD8+ or a CD4+ T cell response.

In alternative embodiments, the antigen specific cytotoxic lymphocyte (CTL) response comprises a carbohydrate specific antigen-specific cytotoxic lymphocyte (CTL) response, or a carbohydrate specific antigen-specific CD8+ CTL response; and/or a carbohydrate specific antigen-specific helper T cell response, or a carbohydrate specific antigen-specific CD4+ T cell response.

In alternative embodiments of the methods, the vaccine is administered parentally or orally, or systemically or topically. The vaccine can be administered via a parenteral route or via a route comprising or consisting of a subcutaneous, an intramuscular, an intravenous (IV), an intradermal, an intramuscular, an intraperitoneal, an intranasal, an intradermal, a transdermal or a buccal route. The vaccine can be administered parenterally by bolus injection or by gradual perfusion over time, or the vaccine can be administered by an oral or a topical route.

In alternative embodiments, the vaccine is administered using a vaccination regime comprising at least one second (booster) administration, or the vaccine is administered at intervals of 1 week, 2 weeks, 4 weeks (or one month), 6 weeks, 8 weeks (or two months) or one year.

In alternative embodiments, wherein the vaccine is administered at a daily dose of glycopeptides (glycoconjugates) in a range of about 10 nanograms to 10 milligrams, or about 1 microgram to 10 milligrams.

In alternative embodiments, the vaccine is administered as a prophylactic or preventative measure to an individual having a personal history of cancer or a family history of cancer, or the vaccine is administered as a prophylactic or preventative measure to an individual having a detected genotype or phenotype indicating a predisposition to a cancer.

In alternative embodiments, the invention provides methods for generating a carbohydrate antigen-specific cytotoxic lymphocyte (CTL) response, and/or a CD8+ T cell response, comprising contacting naïve CTL cells or CD8+ T cells with an effective amount of one or more (at least one) glycopeptides (glycoconjugates) of the invention; the pharmaceutical or formulation of the invention; the liposome of the invention; or the nanoparticle of the invention. In alternative embodiments, the invention provides methods for generating an antigen-specific helper T cell response, and/or a CD4+ T cell response, comprising contacting naïve helper T cells or CD4+ T cells with an effective amount of one or more (at least one) glycopeptides (glycoconjugates) of the invention; the pharmaceutical or formulation of the invention; the liposome of the invention; or the nanoparticle of the invention. In alternative embodiments, the contacting is in vitro or in vivo. In alternative embodiments, the contacting is in vivo to (in) a mammal or a human.

In alternative embodiments of the methods, the T cell response comprises a carbohydrate specific antigen-specific response.

In alternative embodiments, the invention provides methods for lowering prostate serum antigen (PSA) serum levels in an individual in need thereof comprising administering to the individual an effective amount of one or more (at least one) glycopeptides (glycoconjugates) of the invention; the pharmaceutical or formulation of the invention; the liposome of the invention; or the nanoparticle of the invention.

In alternative embodiments, the invention provides methods for inducing (eliciting) an anti-tumor antigen antibody (humoral) B cell response comprising administering to the individual an effective amount of one or more (at least one) glycopeptides (glycoconjugates) of the invention; the pharmaceutical or formulation of the invention; the liposome of the invention; or the nanoparticle of the invention.

In alternative embodiments, the invention provides diagnostic biomarkers for characterizing a specific T-cell response comprising or consisting of one or more (at least one) glycopeptides (glycoconjugates) of the invention; the pharmaceutical or formulation of the invention; the liposome of the invention; or the nanoparticle of the invention. The diagnostic biomarker can comprise one or more (at least one) glycopeptides (glycoconjugates) comprising a detectable tag or label, or other heterologous moiety.

In alternative embodiments, the invention provides glycopeptides of the invention, wherein the peptide is not conjugated (linked) to another peptide.

In alternative embodiments, the invention provides methods wherein the glycopeptide is not administered with another immunogenic or carrier protein.

In alternative embodiments, the invention provides isolated, synthetic or recombinant peptides comprising:

```
FLPDTRFYV,      (SEQ ID NO: 1)
FLFPDTRAV,      (SEQ ID NO: 2)
or
FLFPDTRYV,      (SEQ ID NO: 3)
``` wherein the peptide does not contain a contiguous MUC-1 amino acid sequence greater than 3, 4, 5, 6, 7, 8, 9, or 10 amino acids located adjacent to the amino acid residues at position 1 and position 9 of the peptide.

In alternative embodiments, the invention provides composition consisting essentially of:

```
FLPDTRFYV,      (SEQ ID NO: 1)
FLFPDTRAV,      (SEQ ID NO: 2)
or
FLFPDTRYV,      (SEQ ID NO: 3)
``` and a pharmaceutically acceptable carrier or excipient.

In one embodiment, the invention provides tumor-derived designed glycopeptides (or carbohydrate-peptide conjugates), e.g., 9-mer glycopeptides, comprising specific epitopes of one or more Tumor Associated Carbohydrate Antigens (TACAs). In alternative aspects, the tumor-derived designed glycopeptides of the invention are 5-mer, 6-mer, 7-mer, 8-mer, 9-mer, 10-mer, 11-mer, 12-mer, 13-mer, 14-mer, 15-mer or longer glycopeptides. In one embodiment, the invention provides a composition comprising a tumor-derived polysaccharide (carbohydrate) linked to a peptide, which in alternative embodiments can be a 5-mer, 6-mer, 7-mer, 8-mer, 9-mer, 10-mer, 11-mer, 12-mer, 13-mer, 14-mer, 15-mer or longer. In one embodiment, the carbohydrate moiety of the glycopeptide (carbohydrate-peptide conjugate) of the invention binds with high affinity to a Class I MHC molecule, e.g., a Class I MHC molecule on a T cell such as a cytotoxic T lymphocyte; including HLA molecules in humans and/or comparable Class I MHC molecules in animals. In one embodiment, the carbohydrate moiety of the glycopeptide (carbohydrate-peptide conjugate) of the invention specifically binds to a Class I MHC molecule, e.g., an HLA polypeptide in a human and/or a comparable Class I MHC molecule in an animal.

In one embodiment, the composition is a pharmaceutical composition, e.g., an immunogenic composition, and/or vaccine composition, such as a sterile injectable composition or a spray or powder.

In one embodiment, the tumor-derived glycopeptides (TDGs, or carbohydrate-peptide conjugates) of the invention generate (elicit) a cytotoxic T cell (CTL) (or killer T-cell) response. In one aspect, the TDGs of the invention generate CTL tumor-specific responses against epithelial cell based (epithelial cell-derived) cancers. In one embodiment, the TDGs of the invention generate CTL tumor-specific responses against cancers without requiring helper proteins.

In one embodiment, TACA-containing glycopeptides of the invention are designed to bind with high affinity a variety of class I HLA alleles. In one embodiment, since TACAs are widely expressed on various carcinomas tumor types such as prostate, breast, etc., but not on normal epithelial cells, the glycopeptides described in the present invention are applicable in a large scale population. In one embodiment, the invention further provides that in animal cells, the TACA-specific designer glycopeptides of the present invention are sufficient to generate a cytotoxic response without a T helper (Th), and this CTL anti-tumor response results in regression of tumors from which the TACA are derived.

In one embodiment, glycopeptides (or carbohydrate-peptide conjugates) of the invention bind with high affinity to MHC class I molecules (also called HLA antigens in humans) by comprising a carbohydrate moiety having an appropriate structure (either the same as or sufficiently similar to a TACA) to induce (elicit) a CTL response skewed toward the recognition of the sugar moiety.

The present invention provides for the first time glycopeptides (carbohydrate-peptide conjugates), also called "designer glycopeptides", comprising TACA antigens that can be used as cytotoxic T cell (CTL)-based vaccines for humans or animals. In one embodiment, glycopeptides (or carbohydrate-peptide conjugates) of the invention are designed to bind one or more (multiple) class I HLA polypeptides (also called HLA alleles), or comparable Class I molecules in animals. In one embodiment, the compositions of the invention comprise glycopeptides that bind class I HLA molecules (or comparable Class I molecules in animals) with high affinity to efficiently generate (elicit) cytotoxic T cells (CTLs) in the absence of T helper proteins, T helper peptides and/or strong adjuvants. In one aspect, this can be a great advantage in immunotherapy.

In one embodiment, the invention provides a panel of tumor-derived designer glycopeptides (including non-naturally occurring glycopeptides) comprising the monomer tumor associated carbohydrate antigen Tn (α-GalNAc), a precursor of TF (Thomsen-Friedenreich (TF) antigen, or Gal beta 1-3GalNAc alpha 1-R). In one embodiment, these designer glycopeptides of the invention are derived from the MUC1 glycoprotein, e.g., as with other TACA antigens used in compositions of this invention, the carbohydrate moieties used in the glycopeptide(s) of the invention is/are either the same or sufficiently similar to a TACA to bind to an MHC class I antigen (e.g., an HLA polypeptide) and elicit (generate) an anti-tumor CTL immune response (an immune response against the tumor from which the TACA was derived).

In alternative embodiments, glycopeptides of the invention comprise one, two, three or four or more MUC1-derived designer glycopeptides; and in one aspect a glycopeptide of the invention comprises MUC1-derived designer glycopeptides comprising the TACA antigen Tn (α-GalNAc).

Four (4) glycopeptide MUC1-derived designer glycopeptides was synthesized; and they showed very high affinity for the A2 Human Leucocyte Antigen (HLA) polypeptide (allele). Tn has been used as a TACA model because of its proven high immunogenicity. These exemplary four (4) MUC1-derived designer glycopeptides of the invention comprise the following amino acid sequences: ALG(Tn-S)TAPPV (ALGSTAPPV is SEQ ID NO:4), FLPD(Tn-T)RFYV (FLPDTRFYV is SEQ ID NO:1), FLFPD(Tn-T)RAV (FLFPDTRAV is SEQ ID NO:2), and FLFPD(Tn-T)RYV (FLFPDTRYV is SEQ ID NO:3). Alternative exemplary glycopeptide compositions of the invention comprising carbohydrate moieties (species) derived from natural tumor antigens containing tumor associated carbohydrate antigens (TACA) suitable for cancer immunotherapy (pan-carcinomas) are provided in Table 1, below:

TABLE 1*

| Gene | Position | glycopeptides |
|---|---|---|
| MAGE-A1 | 62-70 | SAFP(Tn-T)TINF (SEQ ID NO: 5) |
| MAGE-A1 | 62-70 | SAFPT(Tn-T)INF (SEQ ID NO: 6) |
| MAGE-A1 | 127-136 | REPV(Tn-T)TKAEML (SEQ ID NO: 7) |
| MAGE-A1 | 161-169 | EADP(Tn-T)GHSY (SEQ ID NO: 8) |
| MAGE-A2 | 127-136 | REPV(Tn-T)KAEML (SEQ ID NO: 9) |
| MAGE-A6 | 290-298 | MVKI(Tn-S)GGPR (SEQ ID NO: 10) |
| Her2/neu | 369-377 | KIFG(Tn-S)LAFL (SEQ ID NO: 11) |
| Her2/neu | 435-443 | ILH(Tn-N)GAYSL (SEQ ID NO: 12) |
| Her2/neu | 789-797 | CLT(Tn-S)TVQLV (SEQ ID NO: 13) |
| p53 | 25-35 | LLPE(Tn-N)NVLSPL (SEQ ID NO: 14) |
| p53 | 25-35 V11 | LLPEN(Tn-N)VLSPV (SEQ ID NO: 15) |
| p53 | 149-157 | LLGR(Tn-N)SFEV (SEQ ID NO: 16) |
| p53 | 149-157 | LLGRN(Tn-S)FEV (SEQ ID NO: 17) |

*In Table 1, Tn has been used as a TACA model, TACA to be linked at the indicated positions; Thomsen-Freidenrich (TF) Tn, sialyl Tn.

In alternative embodiment, glycopeptides of the invention comprise one of the following peptide moieties (in addition to a carbohydrate moiety conjugated thereto):

| | |
|---|---|
| FLPDTRFYV | (SEQ ID NO: 1) |
| FLFPDTRAV | (SEQ ID NO: 2) |
| FLFPDTRYV | (SEQ ID NO: 3) |
| ALGSTAPPV, | (SEQ ID NO: 4) |
| SAFPTTINF, | (SEQ ID NO: 5) |
| SAFPTTINF, | (SEQ ID NO: 6) |
| REPVTTKAEML, | (SEQ ID NO: 7) |
| EADPTGHSY, | (SEQ ID NO: 8) |
| REPVTKAEML, | (SEQ ID NO: 9) |
| MVKISGGPR, | (SEQ ID NO: 10) |
| KIFGSLAFL, | (SEQ ID NO: 11) |
| ILHNGAYSL, | (SEQ ID NO: 12) |
| CLTSTVQLV, | (SEQ ID NO: 13) |
| LLPENNVLSPL, | (SEQ ID NO: 14) |
| LLPENNVLSPV, | (SEQ ID NO: 15) |
| LLGRNSFEV, | (SEQ ID NO: 16) |
| LLGRNSFEV, or | (SEQ ID NO: 17) |
| HGVTSAPDTRPAPGSTAPPA. | (SEQ ID NO: 29) |

In one aspect, the carbohydrate moiety is conjugated to the exemplary peptide as indicated above. In alternative embodiments, the carbohydrate moiety comprises a tumor specific antigen, for example: the disaccharide TF (α-Gal-[1->3]-β-GalNAc); the TF precursor, the monomer Tn (α-GalNAc) or a sialyl moiety. In alternative embodiments, these carbohydrate moieties are conjugated to the peptide as: the disaccharide TF (α-Gal-[1->3]-β-GalNAc-O-serine); the monomer Tn (α-GalNAc-O-serine) or as a sialyl-Tn (STn).

The invention further provides for chemical synthesis of the synthesized designer glycopeptides. In alternative embodiments, the peptide of a glycopeptide of the invention is an isolated, synthetic and/or recombinant peptide.

In one aspect, the invention provides compositions, e.g., vaccines, and methods for using designer glycopeptides of the invention comprising TACAs or similar carbohydrates in cancer therapy, e.g., in carcinoma immunotherapies. In one embodiment, the invention provides a pan-carcinoma vaccine is also made based on the synthesized designer glycopeptides disclosed herewith. Any techniques known to those of skill in the art for producing such designer TACA-specific glycopeptides, including but are not limited to the expression of such designer TACA-specific glycopeptides through standard molecular biological techniques including recombinant techniques, or the chemical synthesis of peptides or proteins are within the scope of the present invention.

In alternative embodiments, the peptide of a glycopeptide of the invention, e.g., a MUC1-derived designer glycopeptide of the invention, are encoded by isolated or recombinant nucleic acids (nucleotides). In alternative embodiments, the invention provides isolated, synthetic or recombinant nucleic acids (nucleotides), homologs and analogs that encode the peptide moieties of glycopeptides of the invention, e.g., encoding peptides comprising amino acid sequences as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof. In alternative embodiments, a nucleic acid encoding a peptide of a glycopeptide of the invention can hybridize at highly stringent conditions to a nucleic acid (nucleotide sequence) encoding an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof. In one aspect, the stringent conditions comprise a wash step comprising a wash in 0.2×SSC at a temperature of about 65° C. for about 15 minutes.

The present invention also provides a pharmaceutical composition comprising a TACA-specific designer glycopeptide of the invention. In one embodiment, the pharmaceutical composition is used for cancer immunotherapy or as a carcinoma vaccine that generates in vivo CD8+ cytotoxic T cells without T helper (Th).

In one embodiment, the invention provides a pharmaceutical composition for cancer immunotherapy. In one embodiment, the invention provides a pharmaceutical composition for use as a carcinoma vaccine that generates in vivo CD8+ cytotoxic T cells. In one embodiment, the pharmaceutical compositions of the invention comprise a MUC1-derived designer glycopeptide of the invention, e.g., a MUC1-derived designer glycopeptide comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof. Such TACA-specific designer glycopeptides, including the MUC1-derived designer glycopeptides, including either the peptide and/or carbohydrate moieties, can be either chemically or recombinantly synthesized, isolated, or produced by any conventional methods known in the art.

The present invention also provides a pharmaceutical composition for cancer immunotherapy, or a carcinoma vaccine, that generates in vivo CD8+ cytotoxic T cells without T helper (Th) involvement; the pharmaceutical composition comprising an isolated, synthetic and/or recombinant TACA-specific designer glycopeptide, e.g., as disclosed herewith (an exemplary glycopeptide of the invention), and a pharmaceutically acceptable carrier or vehicles. In one embodiment, the invention provides a pharmaceutical composition for cancer immunotherapy or a carcinoma vaccine, wherein either can generate in vivo CD8+cytotoxic T cells; in one embodiment the pharmaceutical composition comprises a MUC1-derived designer glycopeptide of the invention, e.g., a glycopeptide comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof, and a pharmaceutically acceptable carrier or vehicles.

The invention further provides a method of providing cancer immunotherapy or a pan-carcinoma vaccine using "designer glycopeptides" of the invention, e.g., isolated, synthetic or recombinant TACA-specific designer glycopeptides. In one aspect, designer glycopeptides can generate a cytotoxic T cell (CTL) response, e.g., a CD8+ CTL response, in vivo without T helper (Th) cells or Th cytokines.

The present invention also provides a method of providing cancer immunotherapy or a carcinoma vaccine using a pharmaceutical composition comprising an isolated, synthetic or recombinant TACA-specific designer glycopeptide of the invention with or with a pharmaceutically acceptable carrier or vehicles. In alternative embodiments the carbohydrate and/or peptide moieties can be in isolated, synthetic or recombinant form. In one embodiment, the invention provides a method of providing cancer immunotherapy or a carcinoma vaccine using a MUC1-derived designer glycopeptide of the invention; e.g., a glycopeptide comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof, with or without a pharmaceutically acceptable carrier or vehicles.

The invention further provides that the isolated, synthetic or recombinant TACA-specific designer glycopeptides of the invention can be administered with a standard adjuvant, such as incomplete Freund adjuvant (IFA), and in an standard administration route, e.g., as intradermal or subcutaneous injections or as powder inhalations. In one embodiment the isolated, synthetic or recombinant glycopeptides of the invention comprises a MUC1-derived glycopeptide comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and/or SEQ ID NO:29; or portions (subsequences) thereof, with or without a pharmaceutically acceptable carrier or vehicles.

In one embodiment, the invention further provides that a stimulated T-cell response in vitro can be used to monitor the effect a vaccine of the invention is having in vivo. In one embodiment, the a TACA-specific designer glycopeptide of the invention can serve as a biomarker for characterizing the specific T-cell subpopulations induced using an immune stimulant, an antigen and/or a vaccine, e.g., a glycopeptide of the invention. In one aspect, conventional assays are used to measure antigen specific T-cell responses. Therefore, in alternative embodiments, designer glycopeptides of the invention are used for diagnostic purposes.

The details of one or more embodiments of the invention are set forth in the description below. Other features, objects, and advantages of the invention will be apparent from the description and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION OF THE INVENTION

Figure 1A:
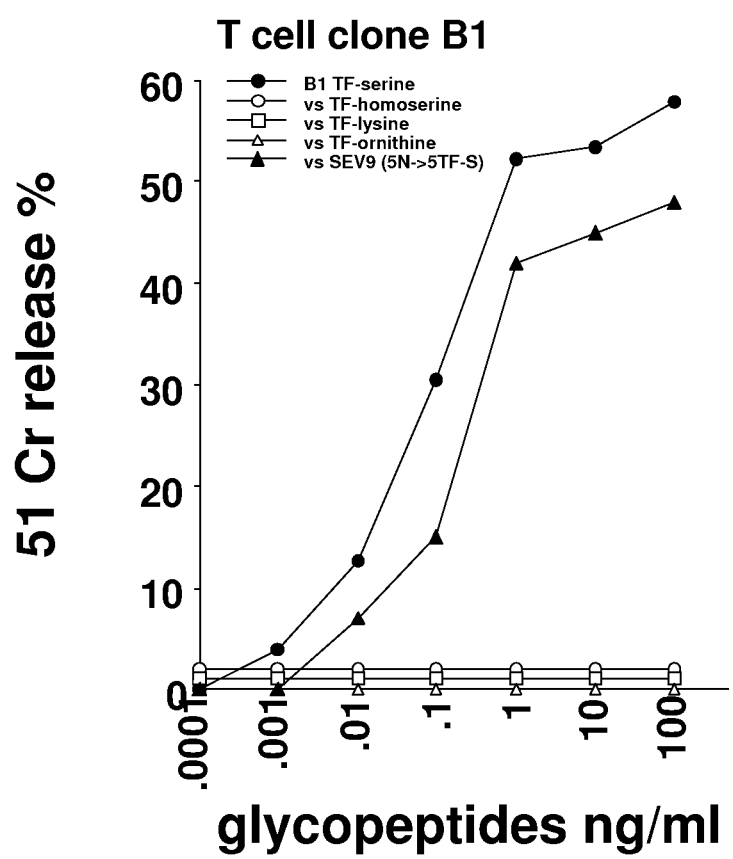
FIG. 1A, FIG. 1B and FIG. 1C illustrate the fine specificity and cross-reactivity of β-Gal-[1->3]-α-GalNAc-O-specific T cell clones, as discussed in detail in Example 2, below.

The invention provides glycopeptides, formulations and vaccines effective for generating cancer antigen specific cell-based and/or humoral (antibody) immune responses. In one embodiment the cancer antigen comprises or consists of a Tumor Associated Carbohydrate Antigen (TACA). In one embodiment, the invention provides glycopeptides (or carbohydrate-peptide conjugates) having carbohydrate moieties comprising TACAs that direct against (e.g., bind specifically to) cytotoxic T lymphocytes (CTLs) or helper T cells for, e.g., CTL- or T-helper-based immunotherapy of a cancer, e.g., a carcinoma, and methods for making and using the glycopeptides of the invention. In one embodiment, the invention provides novel glycopeptides comprising tumor-derived carbohydrate or tumor-derived epitopes that specifically bind to major histocompatibility (MHC) class I molecules on cytotoxic T lymphocytes (CTLs) or MHC molecules on helper T cells, and methods for using same, e.g., as a vaccine.

In one embodiment, the invention provides glycopeptides ("designer glycopeptides") for use as vaccine for generating carbohydrate antigen specific cell-based and/or humoral (antibody) immune responses. In one embodiment, the invention provides glycopeptides (also called glycoconjugates) comprising tumor-derived or "non-normal cell"-derived peptide epitopes. In one embodiment, the invention provides glycopeptides comprising tumor-derived or "non-normal cell"-derived carbohydrates, or "Tumor Associated", Carbohydrate Antigens (TACA). In one embodiment, glycopeptides of the invention comprise tumor-derived antigen peptides, e.g., tumor epitopes, having linked thereto one or more carbohydrates, e.g., TACAs.

In one embodiment, the tumor-associated antigen (TAA) derived peptide of a glycopeptide of the invention is the same or sufficiently similar to a tumor-derived or "non-normal cell"-derived tumor antigen peptide to bind to an MHC Class I polypeptide (e.g., a human HLA antigen, or comparable polypeptide on an animal) and elicit (generate) a tumor specific CTL response; in one aspect, the tumor being that from which the tumor-associated antigen (TAA) was derived or designed from.

In one aspect, the carbohydrate antigen of a glycopeptide of the invention is the same or sufficiently similar to the tumor-derived or "non-normal cell"-derived carbohydrate (e.g., TACA) to bind to an MHC Class I polypeptide (e.g., a human HLA antigen, or comparable polypeptide on an animal) and elicit (generate) a tumor specific CTL response; in one aspect, the tumor being that from which the TACA was derived or designed from. In one aspect, the carbohydrate antigen of a glycopeptide of the invention is the same or sufficiently similar to the tumor-derived or "non-normal cell"-derived carbohydrate (e.g., TACA) to bind to an MHC Class II polypeptide and elicit (generate) a tumor specific helper T cell response; in one aspect, the tumor being that from which the TACA was derived or designed from.

In one aspect, the glycopeptides of the invention are used in cancer immunotherapies and/or pan-carcinoma vaccines.

In one aspect, the glycopeptides of the invention are used in vaccines of the invention as immuno-therapeutics or preventative agents (prophylactics) as pan-tumor vaccines.

In alternative embodiments, glycopeptides of the invention, e.g., TACA-specific designer glycopeptides, comprise 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer or 30-mer or longer glycopeptides.

In alternative embodiments, glycopeptides of the invention elicit a cytotoxic T lymphocyte (CTL) response and/or a helper T cell response. In one aspect, the glycopeptides of the invention elicit a cytotoxic T lymphocyte (CTL) response without T helper lymphocyte (Th) response, e.g., without Th helper proteins.

In alternative embodiments, the glycopeptides of the invention comprise MUC1-derived peptide sequences, and/or MUC1-derived carbohydrates. The MUC1-derived peptide sequences can be MUC1 subsequences, or composite peptides comprising a MUC1 peptide joined to another complete or partial MUC1 sequence. In alternative embodiments, the MUC1-derived peptide sequences can comprise one or several carbohydrate moieties, e.g., two or more of the same TACAs or different TACAs.

In alternative embodiments, glycopeptides comprise an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof. In alternative embodiments, glycopeptides have contained within their sequences a subsequence consisting of one or more tumor epitopes. In alternative embodiments, the two or more tumor epitopes can be multiple copies of the same tumor epitope or different tumor epitopes.

The invention also provides nucleic acids encoding a peptide moiety of a glycopeptide of the invention, including isolated, synthetic and/or recombinant nucleic acids. In one aspect, the invention provides nucleic acids (nucleotides), homologs and analogs thereof encoding TACA-specific designer glycopeptides, including MUC1-derived "designer" glycopeptides of the invention. The invention also provides methods of making and using glycopeptides of the invention, e.g., the TACA-specific designer glycopeptides of the invention, which include analogs thereof.

In one embodiment, the invention provides a pharmaceutical composition, and method of use thereof, for cancer immunotherapy and/or pan-carcinoma vaccine using a glycopeptide of the invention. In one aspect, the glycopeptide of the invention elicits an in vivo CD8+ cytotoxic T lymphocyte (CTL) tumor-specific response and/or a T helper (Th) response tumor-specific response. In one embodiment, the tumor-specific response is specific to a tumor-derived antigen or a TACA. In one aspect, the glycopeptide of the invention elicits an in vivo CD8+ cytotoxic T lymphocyte (CTL) tumor-specific response without a corresponding T helper (Th) response. In one aspect, the glycopeptide of the invention comprises a MUC1-derived "designer" glycopeptide.

In alternative embodiments, the invention provides glycopeptides comprising an amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof. In another embodiment, the invention provides nucleic acids encoding these peptides, including nucleotides, homologs, analogs or complements thereof encoding a glycopeptide of this invention, e.g., a glycopeptide comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof.

In alternative embodiments, glycopeptides of the invention can use subdomains (portions or subsequences) of a glycopeptide comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof. In alternative embodiments, the invention provides nucleic acids encoding these exemplary peptides, including nucleic acids having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, or 100% (complete) sequence identity to the exemplary amino acid (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof and/or exemplary nucleic acid sequence (e.g., encoding SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 or SEQ ID NO:29 or portions (subsequences) thereof) of this invention.

In one embodiment, glycopeptides of the invention comprise one or more (several) tumor associated carbohydrate antigen(s), or TACA(s), and/or one or more (several) tumor epitope peptides. In one embodiment, these TACAs can have a high affinity for a MHC class I molecule (such as a human HLA polypeptide, or comparable animal antigen). In one embodiment, these TACAs can have a high affinity for a MHC class II molecule. In one embodiment, glycopeptides of the invention can generate short-term and/or memory anti-carbohydrate specific cytotoxic T lymphocytes (CTLs) and/or helper T cells. In one embodiment, glycopeptides of the invention can generate short-term and/or memory anti-carbohydrate specific CTLs which do not require T cell help (Th) for their generation and/or activity. In one embodiment, these CTLs and/or helper T cells kill (or assist or "help" in the killing of) TACA-expressing tumors in a classical class I or class II MHC-restricted fashion with high efficiency.

In one embodiment, glycopeptides of the invention comprise tumor associated carbohydrate antigens (TACA) that are expressed as products of aberrant glycosylation; in other words, the carbohydrate moiety of a glycopeptide of the invention can be tumor-specific (expressed on a tumor or abnormal cell) and not expressed on a normal cell, or is expressed in a limited subset of "normal" or non-tumor cells, or is expressed at every low levels on "normal" or non-tumor cells. In one embodiment, the carbohydrate moiety of a glycopeptide of the invention can be from a very early step during neoplastic transformation.

In one embodiment, glycopeptides of the invention have high affinity and/or specific binding to class I MHC molecules such as human HLA polypeptides or comparable molecules on animals. While the invention is not limited by any particular mechanism of action, in one embodiment, because glycopeptides of the invention have a high binding affinity for class I MHC molecules, T cell help (Th) is not required for cytotoxic T cell priming, e.g., as described by Franco et al, Nature Immunology 2000, 1:145.

In one embodiment, glycopeptides of the invention have high affinity and/or specific binding to class II MHC molecules or comparable molecules on animals.

In alternative embodiments, designer glycopeptides of the invention are very short, e.g., are between about 5 to 30 amino acids, or between about 8 to 20 amino acids, e.g., are 5-mer, 6-mer, 7-mer, 8-mer, 9-mer, 10-mer, 11-mer, 12-mer, 13-mer, 14-mer or 15-mer or longer glycopeptides, and therefore not too expensive, thus facilitating vaccination in a large population scale. Evidence that the same tumor associated carbohydrate antigens are expressed on a variety of tumors, e.g., epithelial tumors in the case of TF, Tn and sialyl-Tn, but not in normal cells, supports the efficacy of the pan-carcinoma vaccine effect of the glycopeptides of the invention.

Results of tumor recognition by carbohydrate-specific CD8+ T cell clones generated from wild type C57B1/6 mice immunized with exemplary alanine-rich glycopeptides of this invention comprising Thomsen-Freidenreich antigen (TF), or its monomer Tn, support the efficacy of the glycopeptides of the invention as vaccine compositions. In alternative embodiments glycopeptides of the invention target these two tumor associated carbohydrate antigens (TACA) (TF and Tn) because they are largely expressed in a variety of carcinomas but not in normal tissues; this invention takes advantage of these unique targets for immunotherapy.

In alternative embodiments glycopeptides of the invention are designed to bind with high affinity to molecules of the major histocompatibility complex (MHC), e.g., Class I MHC molecules such as HLA in humans and comparable molecules in animals; see e.g., (2004) J. Experimental Med. 199:707-716.

The same designer glycopeptides previously tested in wild type mice can brake immunological tolerance in mice with well established tumors that express the carbohydrate antigen. As a proof of concept, human carbohydrate-specific CD8+ T cells can also be generated by immunizing in vitro with GalNAc-modified natural viral sequences, used a proof of concept in A2+ normal donors In alternative embodiments, TACA-containing glycopeptides of the invention provide a unique tool to generate cytotoxic T cells (CTLs) in vivo, including CD8+CTLs. In alternative embodiments, TACA-containing glycopeptides of the invention provide a unique tool to generate helper T cells in vivo, including CD4+ lymphocytes. In alternative embodiments, glycopeptides of the invention also generate a tumor-specific humoral (antibody) response. Thus, in these embodiments use of the same vaccine of this invention is effective for a variety of tumors expressing the same tumor-derived or TACA carbohydrate antigen; accordingly, the invention provides compositions and methods for pan-carcinoma immunotherapies.

In alternative embodiments, glycopeptides of the invention comprise TF, Tn and sialyl Tn, which are important receptors on tumor cells for metastasis and invasiveness. In alternative embodiments, glycopeptides of the invention have a high binding affinity for Class I (e.g., HLA molecules in humans and comparable molecules in animals) and/or Class II MHC molecules and comparable molecules in animals. While the invention is not limited by any particular mechanism of action, the high affinity can be due the affinity of the carbohydrate moiety, the peptide moiety and/or the tumor epitope peptide sequence of a glycopeptide of this invention for an MHC molecule (e.g., a Class I and/or Class II polypeptide). In alternative embodiments, these glycopeptides of the invention, e.g., TACA-comprising glycopeptides, are very useful to prevent, decrease the amount or severity of and/or ameliorate tumor metastasis, e.g., after a primary surgery, e.g., in a variety of cancers, such as carcinomas.

In alternative embodiments, glycopeptides of the invention, e.g., TACA-comprising glycopeptides, bind with high affinity Class I MHC molecules (e.g., HLA molecules in humans and comparable molecules in animals), allowing a successful immunization in the absence of adjuvants, antibodies or T helper peptides, providing a great advantage for cytotoxic T cell-based immunotherapy. In alternative embodiments, glycopeptides of the invention, e.g., TACA-comprising glycopeptides, bind with high affinity Class II MHC molecules and/or comparable molecules in animals, allowing a successful immunization in the absence of adjuvants, providing a great advantage for cytotoxic T cell-based immunotherapy.

Polypeptides and Peptides

In alternative embodiments, the invention provides glycopeptides (glycoconjugates) for generating tumor antigen specific cell-based and humoral immune responses in mammals. In one embodiment, a glycopeptide of the invention comprises at least one carbohydrate moiety conjugated (linked) to: a tumor-associated antigen (TAA)-derived peptide, or a peptide comprising or consisting of at least one tumor epitope. In one aspect, the peptide (or polypeptide) is between about 8 to 14 (i.e., 8, 9, 10, 11, 12, 13 or 14), or 8 to 18 (i.e., 8, 9, 10, 11, 12, 13, 14, 15, 16, 17 or 18), or about 6 to 20 (i.e., 6, 7, 8, 9, 10, 11, 12, 13, 14, 15, 16, 17, 18, 19 or 20), or about 5 to 30 (i.e., 5, 6, 7, 8, 9, 10, 11, 12, 13, 14, 15, 16, 17, 18, 19, 20, 21, 22, 23, 24, 25, 26, 27, 28, 29 or 30) or more amino acid residues in length. In one aspect, the at least one carbohydrate moiety is conjugated (linked) to the peptide or at least one tumor epitope at an amino acid residue central to (within) the peptide or tumor epitope.

In alternative embodiments, polypeptides and peptides used to practice the invention (e.g., the polypeptide/peptide moiety of a glycoconjugate of the invention) comprise a recombinant protein, a synthetic protein, a peptidomimetic, a non-natural peptide, or a combination thereof. Peptides and proteins used to practice the invention can be recombinantly expressed in vitro or in vivo. The peptides and polypeptides of the invention can be made and isolated using any method known in the art as well as using the methods described herein. Polypeptide and peptides used to practice the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) including any automated polypeptide synthesis process known in the art.

The glycopeptides and glyco-polypeptides of the invention can be glycosylated in any manner (e.g., N-glycosylated or O-glycosylated) using any technique. The glycosylation can be added post-translationally either chemically or by cellular biosynthetic mechanisms, wherein the later incorporates the use of known glycosylation motifs, which can be added as a peptide motif insert or added in the nucleic acid coding sequence. The glycosylation can be O-linked or N-linked or synthetically attached using any linker, which can be covalent or not.

In alternative embodiments, glycopeptides and glyco-polypeptides of the invention are oligopeptides, peptides, polypeptides or protein sequences, or a fragment, portion, or subunit of any of these or naturally occurring or synthetic molecules, including, e.g., peptidomimetics and non-natural amino acids. In alternative aspects, glycopeptides and glyco-polypeptides of the invention comprise amino acids joined to each other by peptide bonds or modified peptide bonds and may comprise modified amino acids other than the 20 gene-encoded amino acids. The glycopeptides and glyco-polypeptides of the invention may be modified by either natural processes, such as post-translational processing, or by chemical modification techniques that are well known in the art. Modifications can be designed anywhere in the glycopeptides and glyco-polypeptides of the invention, including the peptide backbone, the amino acid side-chains and the amino or carboxyl termini. The same type of modification can be made in the same or varying degrees at several sites in a given peptide/polypeptide.

In alternative embodiments, glycopeptides and glyco-polypeptides of the invention have many types of modifications, e.g., modifications including acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, phosphorylation, prenylation, racemization, selenoylation, sulfation and transfer-RNA mediated addition of amino acids to protein such as arginylation. See for example, Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)). In another embodiment, a DRP can be glycol-pegylated as described in U.S. Pat. No. 7,405,198; or can be glycosylated as described in U.S. Pat. Nos. 7,276,475 or 7,399,613, or 7,338,933, the later describing O-linked glycosylation of peptides. Glycopeptides and glyco-polypeptides of the invention can be acylated as described e.g., in U.S. Pat. No. 7,273,921.

In alternative embodiments, glycopeptides and glyco-polypeptides of the invention can comprise any "mimetic" and/or "peptidomimetic" form. In alternative embodiments, glycopeptides and glyco-polypeptides of the invention comprise synthetic chemical compounds which have substantially the same structural and/or functional characteristics of natural, non-natural and/or tumor polypeptides. A mimetic used to practice the invention can be either entirely composed of synthetic, non-natural analogues of amino acids, or, is a chimeric molecule of partly natural peptide amino acids and partly non-natural analogs of amino acids. A mimetic used to practice the invention can also incorporate any amount of natural or non-natural amino acid conservative substitutions as long as such substitutions also do not substantially alter the mimetic's structure and/or activity (e.g., tumor epitope activity).

Routine experimentation will determine whether a synthetic molecule or mimetic is effective for practicing the invention, e.g., can bind to an MHC polypeptide, or can act as a tumor epitope peptide. Methodologies detailed herein and others known to persons skilled in the art may be used to select or guide one to choose effective mimetic for practicing the compositions and/or methods of this invention.

Polypeptide mimetic compositions for practicing the invention can comprise any combination of non-natural structural components. In alternative aspects, mimetic compositions for practicing the invention can comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY). A polypeptide can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids used to practice this invention can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, e.g., under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics that can be used include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Polypeptides used to practice this invention can comprise tags or signal sequences, i.e., leader sequences, e.g., for identifying or secreting a glycopeptide/glyco-polypeptide used to practice the invention from a production host cell. In one embodiment, a cleavable linker is placed between the signal sequence or tag and the glycopeptide/glyco-polypeptide used to practice the invention.

In one embodiment, the invention provides isolated glycopeptides comprising at least one carbohydrate moiety conjugated (linked) to: a tumor-associated antigen (TAA)-derived peptide, or a peptide comprising or consisting of at least one tumor epitope. Identification of tumor specific polypeptide, antigens and epitopes is well known in the art, and many tumor specific polypeptide, antigens and epitopes are well known in the art. In one embodiment, tumor peptide fragments that are capable of binding to an MHC molecule (e.g., Class I or Class II) and mediating a cell to cell interaction between an APC (the cell expressing the MHC molecule) and a circulating T cell (e.g., a CTL and/or a helper T cell) are tumor epitope peptides used in this invention. In one embodiment, a tumor epitope used to practice this invention is a "T cell epitope" that is protein determinant capable of specific binding to an MHC polypeptide (e.g., a human Class I HLA or a Class II DR polypeptide) and interacting with specific TCRs capable of mediating a tumor antigen-specific immune response. In alternative embodiments, the one tumor epitope used in compositions of this invention are about 3, 4, 5, 6, 7, 8, 9, 10, 11, 12, 13, 14, 15, 16, 17, 18, 19 or more amino acid residues in length. In alternative embodiments, tumor epitopes used in compositions of this invention are T cell epitopes that are linear and do not express specific three dimensional characteristics. In alternative embodiments, tumor epitopes used in compositions of this invention are T cell epitopes are not affected by the presence of denaturing solvents. The invention can use tumor peptide epitopes that can associate with either classical MHC class Ia molecules (HLA-A, B, and C in humans and H2-K, D, and L in mice) in the case of $CD8^+$ T cells, or class II molecules (HLA-DR, DP, and DQ in humans and H2-A and E in mice) for $CD4^+$ T cells.

Methods for identifying tumor epitopes are well known in the art. For example, in alternative embodiments, tumor epitopes used in compositions of this invention are identified using epitope determination procedures, such as e.g., generating overlapping peptide libraries, e.g., as described by Hemmer (1998) Immunology Today 19(4):163-168); Geysen (1984) Proc. Nat. Acad. Sci. USA 81(13):3998-4002; Geysen (1989) Proc. Nat. Acad. Sci. USA 82(1):178-182; Van der Zee (1989) Eur. J. Immunol. 19(1):43-47; and describing algorithms for identifying T cell epitopes is De Groot (1999) Nature Biotechnology 17:533-561); any algorithm or method for identifying tumor epitopes can be used to practice this invention. In another embodiment, a tumor epitope is identified using epitope mapping techniques well known in the art, see, e.g., Epitope Mapping Protocols in Methods in Molecular Biology, Vol. 66 (Glenn E. Morris, Ed., 1996) Humana Press, Totowa, N.J. In one embodiment, linear tumor T cell epitopes used to practice this invention are determined by e.g., concurrently synthesizing large numbers of peptides on solid supports, the peptides corresponding to portions of a protein (e.g., the tumor polypeptide to which it is desired to generate an immune response against), and reacting the peptides with MHC polypeptides or antibodies while the peptides are still attached to the supports. These techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. In one embodiment, conformational epitopes are identified by determining spatial conformation of amino acids such as by, e.g., x-ray crystallography and 2-dimensional nuclear magnetic resonance; see, e.g., Epitope Mapping Protocols described above. In one embodiment, CD4+ T cell binding tumor epitope mapping can be done as described by Delvig, Methods in Molecular Medicine, 10.1385/1-59259-148-5: 349; Chapt 25 page 349, Humana Press. In one embodiment, CD8+ and/or CD4+ T cell binding tumor epitopes are identified and/or confirmed by elution of naturally processed peptides from MHC molecules; e.g., the National Institutes of Health, NIAID, DHHS, maintains an "Immune Epitope Data-Base" (IEDB) that contains data related to antibody and T cell epitopes for humans, non-human primates, rodents, and other animal species, and many MHC Ligand Elution Assays. In one embodiment, tumor epitopes can be eluted as described by Maeurer (1996) Clinical Cancer Res. 2:87-95, where peptides were extracted from HLA-A expressing cells using a pH of 3.3 acid elution, also as described by Storkus (1993) J. Immunol. 151:3719-3727.

In one embodiment, phage display libraries displaying tumor peptide libraries on the phage are used to identify and/or confirm CD8+ and/or CD4+ T cell binding tumor epitopes used to practice this invention, see e.g., D'Mello (2001) J. Immunol. Methods 247(1-2):191-203. Synthetic or pre-made peptide libraries can be used, e.g., pre-made phage display libraries having synthetic peptides from e.g., Creative Biolabs, Port Jefferson Station, N.Y.

Generating and Manipulating Nucleic Acids

In alternative aspects, because the glycopeptides/glycopolypeptides used to practice this invention can be used in recombinant form, the invention provides nucleic acids, which themselves can be recombinant, to make them. In alternative embodiments, nucleic acids of the invention are made, isolated and/or manipulated by, e.g., cloning and expression of cDNA libraries, amplification of message or genomic DNA by PCR, and the like.

The nucleic acids used to practice this invention, whether RNA, cDNA, genomic DNA, vectors, viruses or hybrids thereof, can be isolated from a variety of sources, genetically engineered, amplified, and/or expressed/generated recombinantly. Recombinant polypeptides (e.g., glycopeptide/glyco-polypeptide used to practice the invention) generated from these nucleic acids can be individually isolated or cloned and tested for a desired activity. Any recombinant expression system can be used, including e.g. in vitro, bacterial, fungal, mammalian, yeast, insect or plant cell expression systems.

In one embodiment, nucleic acids used to practice this invention are synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The invention provides and uses fusion proteins and nucleic acids encoding them. Any polypeptide used to practice this invention (e.g., glycopeptide/glyco-polypeptide used to practice the invention) can be fused to a heterologous peptide or polypeptide. In alternative embodiments, a heterologous peptide or polypeptide joined or fused to a protein used to practice this invention can be an N-terminal identification peptide which imparts a desired characteristic, such as fluorescent detection, increased stability and/or simplified purification.

Peptides and polypeptides used to practice this invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle WA). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Pharmaceutical Compositions and Formulations

The invention provides pharmaceutical compositions and formulations comprising glycopeptides of the invention to generate antigen specific cytotoxic T lymphocytes (CTLs) or helper T cells for, e.g., CTL- or T-helper-based immunotherapy of carcinomas. In one embodiment, the invention provides novel glycopeptides comprising tumor-derived carbohydrate or tumor-derived epitopes formulated as a vaccine, e.g., for use as a pan-cancer vaccine.

In alternative embodiments, the compositions of the invention are formulated with a pharmaceutically acceptable carrier. In alternative embodiments, the pharmaceutical compositions and formulations of the invention can be administered parenterally, topically, orally or by local administration, such as by aerosol or transdermally. The pharmaceutical compositions can be formulated in any way and can be administered in a variety of unit dosage forms depending upon the condition or disease (e.g., type of cancer) and the degree of illness, the general medical condition of each patient, the resulting preferred method of administration and the like. Details on techniques for formulation and administration of pharmaceuticals and vaccines are well described in the scientific and patent literature, see, e.g., the latest edition of Remington's Pharmaceutical Sciences, Maack Publishing Co, Easton Pa. ("Remington's").

Glycopeptides of the invention can be administered alone or as a component of a pharmaceutical formulation (composition). The compounds may be formulated for administration, e.g., as a vaccine, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions e.g., vaccine formulations.

Formulations of the compositions of the invention, e.g., vaccine formulations, include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., glycopeptide of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention, e.g., vaccine formulations, can be prepared according to any method known to the art for the manufacture of pharmaceuticals or vaccines. Such drugs can contain sweetening agents, flavoring agents, coloring agents and preserving agents. A formulation or vaccine can be admixtured with nontoxic pharmaceutically acceptable excipients which are suitable for manufacture. Formulations and vaccines may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations, e.g., vaccine formulations, for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions, e.g., vaccine formulations, can contain an active agent (e.g., a glycopeptide or glycol-peptidomimetic of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In one embodiment, oil-based pharmaceuticals are used for administration of hydrophobic glycopeptides of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations, e.g., vaccine formulations, of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In one embodiment, glycopeptides of the invention are formulated as oil-in-water emulsions as described in U.S. Pat. No. 7,371,395, describing an injectable oil-in-water emulsion, comprising an aqueous solution containing at least one immunogen (e.g., glycopeptides of the invention), a mineral oil, a non-ionic lipophilic surfactant and/or a non-ionic hydrophilic surfactant having a high hydrophilic-lipophilic balance (HLB) value. In alternative embodiments, these injectable oil-in-water emulsions of the invention comprise a paraffin oil, a sorbitan monooleate, an ethoxylated sorbitan monooleate and/or an ethoxylated sorbitan trioleate.

In practicing this invention, the pharmaceutical compounds, e.g., vaccine formulations, can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds, e.g., vaccine formulations, can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds, e.g., vaccine formulations, can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds, e.g., vaccine formulations, can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations, e.g., vaccine formulations, of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations, e.g., vaccine formulations, of the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; A1-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In alternative embodiments, for therapeutic applications, compositions are administered to a subject already suffering from a cancer, e.g., a carcinoma, in an amount sufficient to cure, alleviate or partially arrest the clinical manifestations of the cancer, metastasis or its complications, e.g., cancer cachexia; this can be called a "therapeutically effective amount". For example, in alternative embodiments, pharmaceutical compositions of the invention are administered in an amount sufficient to generate an antigen specific cell-based (e.g., CTL or helper T cell) immune response to treat, prevent and/or ameliorate a cancer, a metastasis, a hyperplastic tissue, a granuloma or a tumor. The amount of pharmaceutical composition adequate to accomplish this is defined as a "therapeutically effective dose." The dosage schedule and amounts effective for this use, i.e., the "dosing regimen," will depend upon a variety of factors, including the stage of the disease (e.g., cancer or metastasis) or condition, the severity of the disease or condition, the general state of the patient's health, the patient's physical status, age and the like. In calculating the dosage regimen (e.g., vaccine administration regimen) for a patient, the mode of administration also is taken into consideration, e.g., intradermal injection of vaccine formulation.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations, e.g., vaccine formulations, can be given depending on for example: the dosage and frequency as required and tolerated by the patient, the degree and amount of antigen specific CTLs and/or T helper cells, or antigen-specific antibodies, generated after each vaccine administration, and the like. The formulations should provide a sufficient quantity of active agent to effectively treat, prevent or ameliorate a conditions, diseases or symptoms, e.g., generate an tumor-specific cell-based or humoral immune response.

In alternative embodiments, pharmaceutical formulations, e.g., vaccine formulations, for oral administration are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating cancer, septic shock, infection, fever, pain and related symptoms or conditions. For example, the methods and/or compositions and formulations of the invention can be co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Vaccine Formulations

The invention provides vaccine formulations and methods for making and using them. In alternative embodiments, glycopeptides of the invention are formulated as aqueous solutions and administered intradermally as vaccines.

In one embodiment, vaccine formulations of the invention are administered with an adjuvant appropriate for the individual vaccinated, e.g., whether that individual is a human or an animal. In alternative embodiments, methods for practicing this invention comprise using an amount of adjuvant sufficient to enhance a cell-based and/or a humoral antigen-specific immune response to an immunogen, e.g., a tumor antigen such as a tumor epitope of a glycopeptide of the invention. In one embodiment, adjuvants used to practice this invention are substances capable of non-specifically enhancing or potentiating an immune response.

In alternative embodiments, adjuvants that can be used to practice this invention comprise or consist of incomplete Freund's adjuvant (IFA) or MONTANIDE ISA 51®; alum; aluminum phosphate; aluminum hydroxide; squalene; complete Freund's adjuvant (CFA), or levamisole; QS-21™, or STIMULON® (Antigenic s, Lexington, Mass.); or muramyl dipeptide (MDP) or derivatives thereof; monophosphoryl lipid (MPL) or derivatives thereof; or monophosphoryl lipid A (MPLA) or derivatives thereof; or MF59™ or FLUAD® (Novartis, Basel, Switzerland); or as described in U.S. Pat. No. 7,182,962; or a glycosylceramide as described e.g. in U.S. Pat. No. 7,488,491; triacyl lipid A or derivatives thereof or OM-174™ (OM Pharma, Geneva, Switzerland); or SB-AS2™, or an oil in water emulsion comprising monophosphoryl lipid A (MPLA) and QS-21™; or SYNTEX™ adjuvant formulation (SAF) (Laboratorios Syntex SA, Mexico City Mexico), or an adjuvant comprising a muramyl dipeptide derivative (threonyl-MDP) in an oil-in-water (o/w) emulsion vehicle; or pluronic L121 or poloxamer 401; or a mucosal adjuvant comprising a detoxified mutant A subunit of a cholera toxin (CT) or an E. coli heat labile toxin (LT1 or LT2) as described in U.S. Pat. No. 7,485,304 (Novartis Vaccines and Diagnostics SRL); or an adjuvant as described in U.S. Pat. No. 7,357,936 (SmithKline Beecham Biologicals, SA); or any combination thereof. In alternative embodiments, adjuvants that can be used to practice this invention comprise or consist of aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polyphosphazene and derivatives, and immunostimulating complexes (ISCOMs), e.g., see Takahashi et al. (1990) Nature 344: 873-875.

The immunologically effective amounts of glycopeptides of the invention can be determined empirically, and factors that can be considered include the glycopeptide's immunogenicity, whether or not the glycopeptide will be complexed with or covalently attached to an adjuvant or carrier protein or other carrier, route of administration of vaccine formulation of the invention, and the number of immunizing dosages to be administered. In alternative embodiments, the glycopeptide is not conjugated or linked to another peptide (e.g., an immunogenic peptide) or administered with another protein, such as a carrier protein or immunogenic protein. Such factors are known in the vaccine art and it is well within the skill of physicians and immunologists to make such determinations.

The glycopeptide active agent can be present in the vaccine in varying concentrations, e.g., in one embodiment the minimum concentration of glycopeptide is an amount necessary to generation an initial tumor antigen-specific immune response, while the maximum concentration is the maximum amount that will remain in solution or homogeneously suspended within the initial mixture. In alternative embodiments, the minimum concentration of glycopeptide is an amount necessary to generation an initial tumor antigen-specific immune response and the maximum concentration is the point at which a homogeneous suspension cannot be maintained. In alternative embodiments, doses can comprise 1 to 100 µg of protein antigen, or 5 to 50 µg, or 5 to 25 µg. A desired amount of glycopeptide varies from formulation to formulation, or application to application (e.g., form of cancer to be immunized against) but is easily determinable by one of skill in the art. Vaccine preparation is well known in the art, see e.g., Vaccine Design ("The subunit and adjuvant approach" Eds. Powell M. F. & Newman M. J. (1995) Plenum Press New York).

Methods of delivering the vaccine are also well known in the art. For example, in alternative embodiments vaccines of the invention are formulated and delivered via a parenteral route comprising or consisting of a subcutaneous, an intravenous (IV), an intradermal, an intramuscular, an intraperitoneal, an intranasal, a transdermal or a buccal route.

In alternative embodiments vaccines of the invention are delivered intradermally or intra-epidermally using any needle-like structures or device, e.g., as described in U.S. Patent App. Pub. No. 20090012494, describing use of microneedle devices, e.g., with rows of hollow microneedles. In alternative embodiments vaccines of the invention are delivered using micro-cannula, e.g., as described in U.S. Pat. No. 7,473,247. When using this or another device or needle to practice this invention, vaccine formulations can be directly targeted into an intradermal space; or can be delivered into an intradermal space as a bolus or by infusion. In alternative embodiments, "intradermal" is administration of a vaccine formulation of this invention into the dermis in such a manner that the glycopeptide of the invention therein readily reaches the richly vascularized papillary dermis where it can be rapidly systemically absorbed, or the vaccine can be taken up directly by cells (e.g., dendritic cells) in the skin. In alternative embodiments, "intradermal" includes every layer of the skin, including stratum corneum, epidermis and dermis.

In one embodiment, a drug-delivery patch is used to deliver a vaccine formulation of this invention, e.g., as described in U.S. Patent App. Pub. No. 20090010998. In one embodiment, the invention provides a drug-delivery patch having at least one dissolvable layer comprising a glycopeptide of the invention and an adhesive backing or cover. In one embodiment, an individual is transdermally vaccinated by ablating an area of the stratum corneum of the individual and applying the patch to that area.

In one embodiment, a glycopeptide of the invention is delivered via dendritic cell administration, e.g., as described in U.S. Patent App. Pub. No. 20090010948. In one embodiment, a glycopeptide of the invention is formulated as a dendritic cell (DC)-based tumor vaccine; this modality is a well-known therapeutic approach for generating immune responses and for cancer treatment; see e.g., Schuler (2003) Curr. Opin. Immunol. 15(2):138-47; Dallal (2000) Curr. Opin. Immunol. 12(5):583-8; Steinman (2001) Int J. Cancer. 94(4):459-73. In practicing this embodiment, DCs can deliver not only the tumor antigen contained within a glycopeptide of this invention, but the DC also can be a natural adjuvant to boost the vaccine's efficiency. DCs also can provide critical molecules, cytokines or co-stimulatory signals to the T cells they interact with during activation.

Methods for determining the efficacy of a vaccine formulation of this invention, or a particular administration of a vaccine formulation of this invention, are well known in the art. For example, cell-based or humoral responses can be assessed (measured) using in vitro based assays and/or in vivo based assays, including animal based assays. Assays for measuring cell-based or humoral immune response are well known in the art, e.g., see, Coligan et al., (eds.), 1997, Current Protocols in Immunology, John Wiley and Sons, Inc. Cell-based or humoral immune responses may be detected and/or quantitated using standard methods known in the art including, e.g., an ELISA assay, chromium release assays and the like. The humoral immune response may be measured by detecting and/or quantitating the relative amount of an antibody which specifically recognizes an antigenic or immunogenic agent in the sera of a subject who has been treated with a vaccine formulation of this invention relative to the amount of the antibody in an untreated subject. ELISA assays can be used to determine total antibody titers in a sample obtained from a subject treated with an agent of the invention.

Kits and Packages

The invention provides kits, packets and packages comprising compositions and cells (e.g., dendritic cells) of this invention and, in some aspects, instructions for practicing methods of the invention, including the vaccine formulations or drug-delivery patches of this invention. In alternative embodiments, storage devices, such as vials, and glycopeptide delivery devices such as drug-delivery patches comprising glycopeptide formulations of the invention are provided herein.

These and many other variations and embodiments of the invention will be apparent to one of skill in the art upon a review of the appended description and examples. The invention will be further described with reference to the following examples; however, it is to be understood that the invention is not limited to such examples.

EXAMPLES

Example 1

Glycopeptides Containing Tumor Associated Carbohydrate Antigens (TACA) as CTL-Based Preventive Vaccine for Carcinomas This example presents data demonstrating that compositions of the invention effectively generate anti-tumor cell-based immune responses.

Glycopeptides containing tumor associated carbohydrate antigens (TACA), having high affinity for MHC class I molecules have been found to generate short-term and memory anti-carbohydrate specific cytotoxic T lymphocytes (CTLs) in mice, which do not require T cell help (Th). These T cells kill with high efficiency TACA-expressing tumors in a classical class I MHC-restricted fashion. This study aims at optimizing the design of peptide backbones for carbohydrate conjugation in the A2 human class I allele model for preclinical trials.

It is an object of this study to optimize carbohydrate-peptide conjugates that bind with high affinity to MHC class I molecules and have an appropriate structure to induce a T cell response skewed toward the recognition of the sugar moiety. Accordingly, the study includes: 1) optimal binding affinity to MHC class I molecules; and 2) sequences containing serine or threonine at predicted TcR contacts, e.g., at positions 4, 5 and 6.

The synthesis of four exemplary Tn-containing glycopeptides of this invention has been successfully completed: a designer, alanine-rich peptide backbone and three natural viral sequences derived from non-environmental pathogens (HBV and HIV viruses). The costs and yield of compounds with high degree of purity (≥97%) has been reasonable, demonstrating that this vaccination avenue is feasible in a large population scale. The A2 affinity of the three glycopeptides derived from natural sequences resulted higher than corresponding peptide backbones ($K_D=\leq 10$ nM), confirming the concept that TACA-conjugation at major T cell receptor contact residues does not affect class I MHC binding. Moreover, class I MHC binding has been retained when three common A2 subtypes have been tested (A*0201, A*0203, A*0206). The alanine-rich glycopeptide binds A2 molecules and its variants with an affinity slightly higher than the corresponding peptide but still efficiently. Immunogenicity studies in 9 normal donors suggested that glycopeptides derived from the three natural viral sequences are preferable to the designer glycopeptide in obtaining TACA-specific CTL responses, notably not reflecting results previously obtained in the murine $K^b$ model, see e.g., (2004) J. Expt. Med. 199:707.

Many TACA-specific T cell lines were found to recognize the peptide backbone, suggesting that to expand a truly naïve CTL population skewed to the TACA molecules it would be advantageous to generate glycopeptides containing a designer "core" for CTL recognition in addition to class I MHC anchors. Accordingly, designer MUC1-derived epitopes containing the "PDTR" fragment of the variable number of tandem repeat (VNTR) domains of MUC1 were synthesized. The "PDTR" fragment has been found immunodominant in B cell- and T cell-responses to the MUC1 glycoprotein, where T in position 5 or 6 is a major TcR contact. "PDTR"-containing glycopeptides have been designed to incorporate primary and secondary anchor residues for optimal binding to A2 class I MHC molecules. The A2 binding affinity of these glycopeptides was determined ($K_D \leq 4$ nM). These designer glycopeptides have been chosen in substitution to the initially proposed Flu-derived determinants.

These results demonstrate that CTL are capable of recognizing tumor-associated carbohydrate antigens (TACA) in the context of glycopeptides with high affinity for class I MHC molecules in animals (e.g., mice) and humans, e.g., in the context of glycopeptides of this invention. In alternative embodiments, glycopeptides of this invention result in super-agonistic epitopes which are more immunogenic than corresponding peptides. These studies further aim at defining the best peptide backbone strategy for TACA conjugation.

To optimize for preclinical trials glycopeptides vaccines, the monomer Tn was targeted because it is largely expressed in several epithelial tumors; thus, one glycopeptide of this invention used as a cancer vaccine can generate a sustained CTL response and be effective in preventing and/or treating (ameliorating) a variety of carcinomas on a large population scale.

Example 2

Glycopeptides Containing Tumor Associated Carbohydrate Antigens (TACA) as CTL-Based Preventive Vaccine for Prostate Cancer This example presents data demonstrating that compositions of the invention effectively generate anti-tumor cell-based immune responses. In particular, this example demonstrates that exemplary designer glycopeptides vaccine of this invention comprising a tumor associated carbohydrate antigen (TACA) Tn (α-GalNAc) can effectively generate (elicit) a CD8+ cytotoxic T cell-based immunotherapy for a prostate cancer. In one embodiment, the invention provides a therapeutic/preventive vaccine for use to treat/prevent metastasis in prostate cancer patients; where the vaccine comprises at least one exemplary glycopeptide of this invention comprising a tumor associated carbohydrate antigen (TACA) Tn (α-GalNAc), and the vaccine can effectively elicit a cytotoxic T cell-based anti-tumor immune response.

In alternative embodiments, vaccines of this invention target TACAs, e.g., the exemplary vaccine of the clinical trial described in this example that targets the Tn antigen, or any TACA expressed in a variety of carcinomas.

A Phase 1 clinical trial using an exemplary vaccine of this invention was designed for use in prostate cancer patients, where the vaccine comprised glycopeptides epitopes to induce a strong primary and memory cytotoxic T cell (CTL) responses. This exemplary vaccine of this invention, as with all vaccines of this invention, may be used as pan-carcinomas vaccines in a large population.

In one aspect, the vaccination protocol involves a single, low dose of glycopeptide having minimal epitopes, e.g., 9 amino acid long. In one aspect, a single dose of glycopeptides at 0.5 mg each, 1.5 mg the pool of three is administered. In one aspect, the vaccine protocol includes 3 injections, 4 weeks apart. The study includes the measurement of primary and memory cytotoxic T cell responses to the Tn carbohydrate antigen and the ability of Tn-specific T cells to recognize Tn-expressing tumors in vitro.

In one aspect, vaccines of the invention are administered with an adjuvant, e.g., an adjuvant that comprises or consists of alum, aluminum phosphate, aluminum hydroxide, squalene, Freund's adjuvant, complete Freund's adjuvant (CFA), incomplete Freund's adjuvant (IFA), or levamisole; QS-21™, or STIMULON® (Antigenics, Lexington, Mass.), and the like. Peptides in IFA containing exemplary sequences (e.g., a MUC1 core motif) have been tested in clinical trials and have been proven safe and well tolerated in cancer patients, see Table 4, below.

Tn, a carbohydrate molecule targeted in an exemplary vaccine of this invention has been tested and proven safe in a variety of clinical trials aimed at generating Tn-specific antibodies in cancer patients, including prostate cancer patients, see e.g., Table 5, below. See also a summary of previous Tn-based clinical trials in Franco, A., (2008) Medical Chemistry 8:86-91.

Designer Glycopeptides Restricted by the Murine $H-2^b$ Molecule

These studies were performed in vivo by injecting Tn-containing glycopeptides in: 1) wild type mice (C57BL/6, $H-2^b$); and 2) MUC1/MT double transgenic mice ($H-2^b$) that develop spontaneous tumors expressing the Tn carbohydrate molecule within 12 weeks of age. Both strains generated a robust cytotoxic T cell response skewed toward the carbohydrate molecule and capable of killing a variety of tumors in vitro.

Designer Glycopeptides Restricted by the Human class I HLA-A2 Molecule

In this category studies were performed in vivo by injecting Tn-containing glycopeptides in: 1) A2/K$^b$ transgenic mice (C57BL/6 that express the human A2 class I HLA molecule; and 2) MUC1/MT/A2/K$^b$ triple transgenic, generated by our group, that develop spontaneous tumors expressing the Tn carbohydrate molecule and human HLA-A2 molecules.

A robust cytotoxic T cell response was detected. The T cell response showed a high degree of carbohydrate recognition. Recognition of amino acid residues within the peptide backbone also occurred.

Unlike in the entirely murine system studied with K$^b$-restricted epitopes, these mouse/human systems do not lend themselves to useful results about the efficacy of A2-restricted glycopeptides for human studies. An additional problem in using triple transgenic MUC1/MT/A2/K$^b$ mice as vaccine recipients is the large breeding effort necessary to achieve a sufficient number of animals, age matched, for valuable results. Due to these limitations, these two in vivo systems were not used to test whether or cytotoxic T cells derived from those strains would kill tumor expressing the Tn antigen being restricted by the human HLA-A2 molecule.

A2/K$^b$ transgenic mice have been successfully used to test the efficacy and perform toxicology studies on peptides that were subsequently used in T cell-based cancer immunotherapy Phase 1 clinical trials.

Our data show that exemplary "designer" glycopeptides of this invention are highly immunogenic in both the murine and the HLA transgenic combination. In both instances anti-carbohydrate T cell responses were generated. In addition, in HLA-A2 transgenic mice we found that CD8 T cells responses against the peptide backbone could also be induced.

Immunization Studies in MUC1/MT Transgenic Mice (H-2$^b$)

These experiments proved 1) circumvention of tolerance, and 2) induction of tumor killing by cytotoxic T cell clones after vaccination with K$^b$-restricted glycopeptides. We also found that older mice with well-established tumors were capable of responding to glycopeptides vaccines (see below), demonstrating that glycopeptides of this invention are useful compositions for immuno-therapeutics in patients with advanced cancer; because (although the invention is not limited by any particular mechanism of action), in some embodiments glycopeptides of this invention are capable of breaking immunological tolerance.

In Vitro Immunization Studies Using Human Peripheral Blood Lymphocytes

Supporting evidence that exemplary "designer" glycopeptides of this invention can be effective in eliciting the expansion of carbohydrate-specific CD8 T cell precursors was obtained by priming in vitro peripheral blood mononuclear cells (PBMC) from normal A2+ donors by culturing autologous dendritic cells (DC) as antigen presenting cells (APC) for glycopeptides presentation (see below).

The TACA Tn (α-GalNAc) was Used as a Hapten Model

We designed minimal (9mer) epitopes, derived from well-known immunodominant viral sequences, chosen for their high affinity for class I MHC molecules (HLA-A2) and because carrying a suitable amino acid for O-glycosylation (S or T) in a central position within the sequence, corresponding to a major T cell epitope. Glycopeptides were more immunogenic than peptides and class I MHC binding was retained.

These data (see below) support the efficacy exemplary "designer" glycopeptide vaccines of this invention in (for treating, preventing) carcinomas, e.g., prostate cancer patients.

Exemplary "designer" glycopeptides of this invention, e.g., Tn-containing glycopeptides, can have an important therapeutic outcome in preventing metastasis in cancer patients, e.g., prostate cancer patients, with a profound impact in their prognosis.

Exemplary "designer" glycopeptides of this invention comprise relevant tumor-specific antigens from a variety of tumor types. In alternative embodiments, the carbohydrate tumor antigens used in the compositions of this invention are not tissue-specific; but rather do share antigenic patterns to allow the generation of a preventive/therapeutic vaccine in a large tumor population.

In alternative embodiments, "designer" glycopeptides of this invention comprise a group of tumor-associated carbohydrate antigens that have been identified and characterized by virtue of their reactivity with antibodies and lectins; the so-called tumor-associated carbohydrate antigens (TACA). In alternative embodiments, "designer" glycopeptides of this invention comprise TACAs that are broadly expressed, e.g., as a product of aberrant glycosylation, e.g., as in a large number of tumors; thus, the compositions (e.g., vaccines) of the invention are a unique tool for prophylactic and/or therapeutic vaccination. In alternative embodiments, "designer" glycopeptides of this invention comprise carbohydrate antigens that are "aberrantly glycosylated"; e.g., comprise TACA expressed in neoplastic cells. Thus, the compositions (e.g., vaccines) of the invention can influence (modify, improve) the prognosis and survival of cancer patients.

In alternative embodiments, "designer" glycopeptides of this invention target prostate cancer and the variety of "non-normal" or aberrant TACA antigens glycoproteins and/or glycolipids on these cancer cells. In alternative embodiments, "designer" glycopeptides of this invention target the small monomer Tn (GalNAc-O-), which is frequently present on the cell surface of primary tumors and metastasis. In alternative embodiments, "designer" glycopeptides of this invention target the Thomsen-Friedenreich (TF) antigen (α-Gal-[1->3]-β-GalNAc-O-), which is a disaccharide that contains Tn.

Because of the small size and broad expression of Tn and TF during an early stage of cancer transformation in several tumor types, in alternative embodiments glycopeptides of this invention effectively target prostate, bladder, colorectal, gastrointestinal, ovarian and lung carcinomas. In alternative embodiments, vaccines of this invention target TF and Tn as targets for a CTL-based vaccine in a large scale.

In alternative embodiments, vaccines of this invention target carbohydrate antigens in tumors for cancer immunotherapy, and can prevent or reduce or ameliorate the amount or severity of metastasis. Because TACA targeted by vaccines of this invention are not only tumor markers, but constitute essential cellular machinery to induce metastasis and invasiveness, vaccines of this invention can prevent or reduce or ameliorate the amount or severity of metastasis.

The invention elucidates the immunochemical requirements for recognition of carbohydrate antigens by mouse and human CD8+ cytotoxic T cells. In alternative embodiments, vaccines of this invention can generate carbohydrate-specific CTL cells that recognize and respond to carbohydrates. In alternative embodiments, vaccines of this invention can generate primary and memory anti-tumor CD8+ T cell responses in cancer patients, e.g., prostate cancer patients, after vaccination with glycopeptides of this invention.

In alternative embodiments, vaccines of this invention use Tn TACA antigen, which is useful as a target antigen because of its high immunogenicity. Fine specificity studies in a variety of TF-specific T cell clones demonstrated that Tn is an immunodominant carbohydrate molecule for T cell recognition. Tn linked to immunogenic proteins, given in a trimer or cluster, has been successfully targeted in phase 1 clinical trials for the generation of antibody responses not only in prostate carcinomas, but also in ovarian, breast and colon carcinomas.

In alternative embodiments, vaccines of this invention comprise vaccine preparations comprising a mixture of 3 glycopeptides emulsified in MONTANIDE ISA 51® adjuvant (MONTANIDE®, Seppic Inc., Fairfield, N.J.). The route of administration can be subcutaneous (s.c.) injection. In alternative embodiments, glycopeptide concentrations in the vaccine are 0.5 mg/ml for each glycopeptide, 1.5 mg/ml total glycopeptide concentration. The glycopeptide vaccine will be tested in a proof of principle Phase 1 study in HLA-A2+, prostate serum antigen (PSA) only, patients with prostate cancer.

The glycopeptides included in the study are three exemplary glycopeptides of this invention: so-called "designer" MUC1-derived epitopes containing the "PDTR" fragment of the variable number of tandem repeat (VNTR) domains of MUC1; the "PDTR" fragment has been found immunodominant in B cell- and T cell-responses to the MUC1 glycoprotein (see e.g., Brossart (1999) Identification of HLA-A2-restricted T-cell epitopes derived from the MUC1 tumor antigen for broadly applicable vaccine therapies. Blood 93:4309).

Our extensive T cell clonal studies, in agreement with reported A2/peptide(s) crystals, suggested that T in position 4, 5 or 6 is a major TcR contact, therefore ideal for Tn conjugation.

In addition to toxicity and tolerability, the study will assess the induction of Tn antigen-specific primary and memory CTL responses. Although not a primary end-point of the study we will also look at the effect of vaccination in lowering PSA levels, or decreasing the doubling time against historical controls.

All three exemplary glycopeptides of this invention have been designed to bind with high affinity several A2 class I MHC molecules subtypes (supertype motifs) and have an appropriate structure to induce cytotoxic T cell responses skewed toward the exclusive recognition Tn in the absence of peptide backbone recognition.

For this study, and in some embodiments, the criteria for inclusion are: a high binding affinity to MHC class I molecules and peptide sequences containing serine or threonine at predicted TcR contacts, positions 4-6.

For this study, and in some embodiments, parameters to be considered in designing glycopeptides of this invention with high binding affinity for A2 molecules are: 1) optimal length and the presence of critical anchor residues; 2) maintenance of a peptide backbone to allow hydrogen bonding between main chain atoms in the peptide and in the atoms in the MHC molecules; and 3) avoidance of detrimental residues at non-anchor positions that interfere with the docking of the peptide in the MHC binding groove. These parameters have been considered by constructing the Tn-containing glycopeptides to be used as vaccines in prostate cancer patients.

A Phase 1 study can be in HLA-A2+ prostate cancer patients with only prostate serum antigen (PSA) recurrence. In addition to toxicity and tolerability, a study can assess the induction of primary and memory Tn antigen-specific CTL responses and their effects on PSA levels. Glycopeptides can be injected as a pool subcutaneously (s.c.) in MONTANIDE ISA 51® adjuvant (MONTANIDE®, Seppic Inc.), IFA or any other adjuvant depending on the individual immunized (e.g., whether animal or human).

Manufacture and Dose Form

In alternative embodiments, the vaccine drug product is a preservative-free, sterile emulsion of three (3) synthetically manufactured glycopeptides, an aqueous/DMSO buffer system and MONTANIDE ISA 51®.

In one embodiment, the route of administration is by subcutaneous injection. Glycopeptide concentrations in the vaccine can be 0.5 mg/ml for each glycopeptide, 1.5 mg/ml total glycopeptide concentration. The primary container can be a rubber stoppered, glass vial (preclinical safety supplies) or glass pre-filled syringes (clinical supplies).

In one embodiment, the length of each of glycopeptides is 9 amino acids. In one embodiment, glycopeptides are manufactured synthetically by solid-phase (e.g., Merrifield), fmoc chemistry, isolated and purified as the acetate salt.

In one embodiment, synthetic glycopeptides are in incomplete adjuvant and used in a repeated dose administration: 5× in humans.

In one embodiment, glycopeptide vaccines of this invention induce a strong and robust T cell response against a viral carbohydrate antigen or a tumor-specific carbohydrate antigen, e.g., the carbohydrate antigen Tn.

Prostate cancer and many other carcinomas display a variety of TACA antigens glycoproteins and/or glycolipids. In particular, the small monomer Tn (GalNAc-O-) that is always present on the cell surface of primary tumors and metastasis as well as the Thomsen-Friedenreich (TF) antigen (α-Gal-[1->3]-β-GalNAc-O-), the disaccharide that contains Tn. The generation of primary and memory cytotoxic T cell response to Tn is the scope of the proposed vaccination.

In one embodiment, glycopeptide vaccines of this invention are TF- and/or Tn-comprising glycopeptides vaccines for CD8+ T cell-based immunotherapy. In one embodiment, the vaccine drug product of this invention a preservative-free, sterile emulsion; e.g., of one or several, e.g., 1, 2, 3, 4, 5, or more synthetically manufactured glycopeptides of the invention, e.g., in an aqueous/DMSO buffer system and an adjuvant, e.g., MONTANIDE ISA 51® (Seppic Inc.).

In alternative embodiments, the route of administration is by intradermal, subdermal or subcutaneous (s.c.) injection. In alternative embodiments, glycopeptide concentrations in the vaccine are 0.1, 0.2, 0.3, 0.4 or 0.5 or more mg/ml for each glycopeptide, e.g., 1.5 mg/ml total glycopeptide concentration. The primary container can be a rubber stoppered, glass vial (preclinical safety supplies) or glass pre-filled syringes (clinical supplies). In alternative embodiments, each (one or all) of the glycopeptides is 5, 6, 7, 8, 9, 10, 11, 12, 13, 14 or more amino acids in length. In alternative embodiments, each (one or all) of the glycopeptides is manufactured synthetically by solid-phase (Merrifield), fmoc chemistry, isolated and purified as the acetate salt.

MONTANIDE ISA 51® (Seppic Inc.) is a commercially available vaccine adjuvant containing mineral oil and surfactant. MONTANIDE ISA 51® can be specifically formulated to form stable, water-in-oil emulsions and is manufactured and distributed by Seppic, Inc., Fairfield, N.J. The vial and pre-filled syringe products can be stored either individually or in secondary packaging (fiber board container) under refrigeration (e.g., 5 to 10° C.).

Non Clinical Developmental Program and Pharmacology

Preclinical Characterization

In one aspect, the invention uses minimal epitopes with high affinity for class I MHC molecules by carrying a carbohydrate hapten in a central position on a peptide; in one embodiment the peptide corresponds to a major T cell epitope.

In one aspect, carbohydrate hapten-specific T cell responses generated in practicing this invention, although "conventionally" MHC restricted, are relatively less dependent on MHC contacts. This can be a great advantage in immunotherapy, particularly with vaccines of this invention comprising T cell epitopes capable of binding multiple MHC alleles; these vaccines of this invention can be applicable in a large population.

We also proved that the binding affinity of the cytotoxic T cell epitope to class I HLA molecules determine the requirement for T cell help (Th). By using an alanine-rich $K^b$-restricted glycopeptide ($K^b$ binding capacity IC50=7 nM), containing the disaccharide TF in position 5, we could generate primary and memory TF-specific cytotoxic T cells in C57BL/6 mice in the absence of Th, a great advantage for cytotoxic T cell-based vaccine formulation.

By using small tumor associated carbohydrate antigens, we proved that carbohydrate-specific T cells recognize a variety of tumors in vitro that express the carbohydrate antigen. The high cross-reactivity of the T cell repertoire allows recognition of carbohydrate expressed in the context of endogenous peptides of unknown sequence.

We defined the TACA Tn ($\alpha$-GalNAc), largely expressed in carcinomas, as the most immunogenic for cytotoxic T cell based immunotherapy probably because of its small size and stable presentation by MHC molecules. Tn is also recognized by TF-specific T cells, further stressing its relevance as a vaccine target in carcinomas, representing the critical TcR contact for T cells capable of recognizing larger sugar molecules. These results also prove the exclusive TcR specificity within carbohydrate molecules.

Cross-Reactivity and Fine Specificity of $\alpha$-Gal-[1->3]-$\beta$-GalNAc-O-specific CTL Clones In one embodiment, vaccines of the invention generate TACA-specific T cell clones that recognize carbohydrate antigens in the context of different peptide sequences; this can be significant because the sequences of endogenous peptides presenting carbohydrate antigens on prostate tumor cell surfaces in vivo are unknown.

CTL clones were generated in C57BL/6 mice (H-$2^b$) immunized with a $K^b$-restricted designer alanine-rich glycopeptide sequence that contained TF, sequence:

AIIA($\beta$-Gal-[1->3]-$\alpha$-GalNAc-O-serine)FAAL

TF-specific CTL clones were tested for the capacity to cross-react to a glycopeptide with a completely unrelated sequence but carrying the sugar at the same position (5 within a 9mer). For this analysis, we designed a modified Sendai virus immunodominant epitope NP 324-332 (5N->5S-TF), sequence:

FAPG ($\beta$-Gal-[1->3]-$\alpha$-GalNAc-O-S)YPAL

This epitope is an ideal proof concept because when bonded to $K^b$ class I MHC molecules it exposes position 5 as a major TcR contact.

To define the role of the glycosylated amino acid linker for sugar recognition by T cells, the same T cell clones were also tested for cross-reactivity to three alanine-rich glycopeptides with identical sequences as the immunogen: AIIA($\beta$-Gal-[1->3]-$\alpha$-GalNAc-O-serine)FAAL, but where TF was linked to different amino acid residues.

Lysine (K), ornithine (O), or homoserine (hs) containing glycopeptides were chosen because of their long side chains, which are potentially more immunogenic than serine, while "bulging out" of the MHC binding groove. Lysine has been successfully used to generate hapten-specific CTL responses in our very initial studies.

T cells were studied with a classic $^{51}$Cr release cytotoxicity assay at a 5:1 effector/target (E/T) ratio. The EL-4 thymoma cell line (H-$2^b$), class II MHC negative, was used as the target in these experiments. The cytolytic response to EL-4 cells in the absence of glycopeptides (background) was also assayed, and subtracted, to quantify the net specific lysis. None of the T cell clones recognized the peptide backbone, stressing again the success of this invention's vaccine in skewing the response toward the sugar moiety, see FIG. 1.

T cell clones have high affinity/avidity for the $\beta$-Gal-[1->3]-$\alpha$-GalNAc-O-serine glycopeptide immunogen, see FIG. 1, filled circles. In terms of cross-reactivity, carbohydrate-specific T cell clones showed good cytolytic activity in response to the glycopeptide derived from Sendai NP 324-332, see FIG. 1, filled triangles, supporting the importance of the core of the peptide (e.g., position 5 in a 9-mer) for TcR contacts and the impressive cross-reaction of the TF-serine specific CTL repertoire primed in vivo with the exemplary alanine-rich glycopeptide.

The results of the cross-reactivity of the T cell clones against alanine-rich glycopeptides with an identical sequence, e.g., an immunogen carrying non-natural amino acid linkers for TACA conjugation, were striking: CTL clones did not cross-react with either a homoserine-alanine-rich glycopeptide (FIG. 1, empty circles) or with a lysine-alanine-rich glycopeptide (FIG. 1, empty squares), or with an ornithine-alanine-rich glycopeptide (FIG. 1, empty triangles).

Figure 1B:
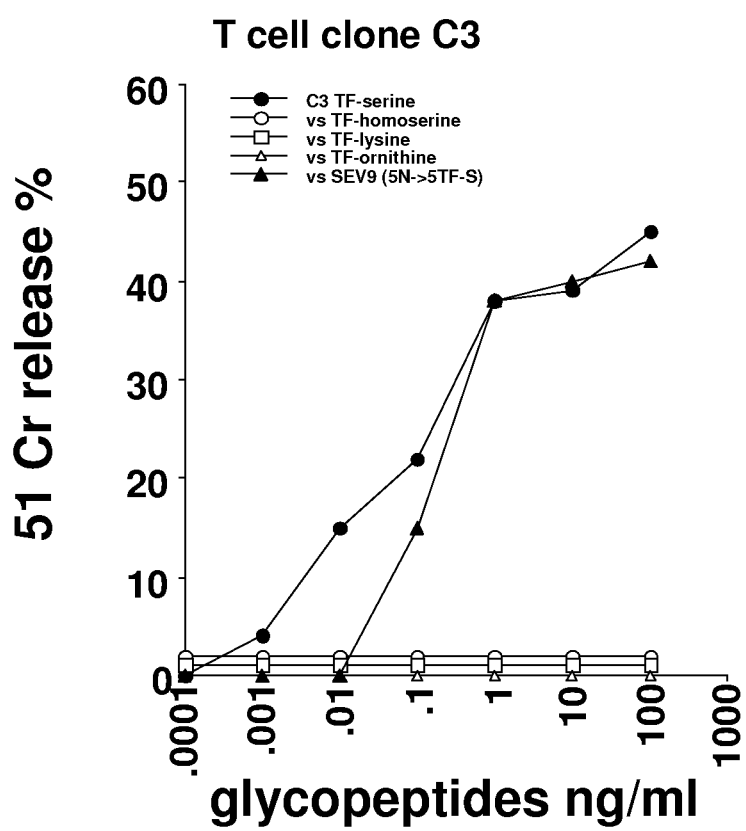
Figure 1C:
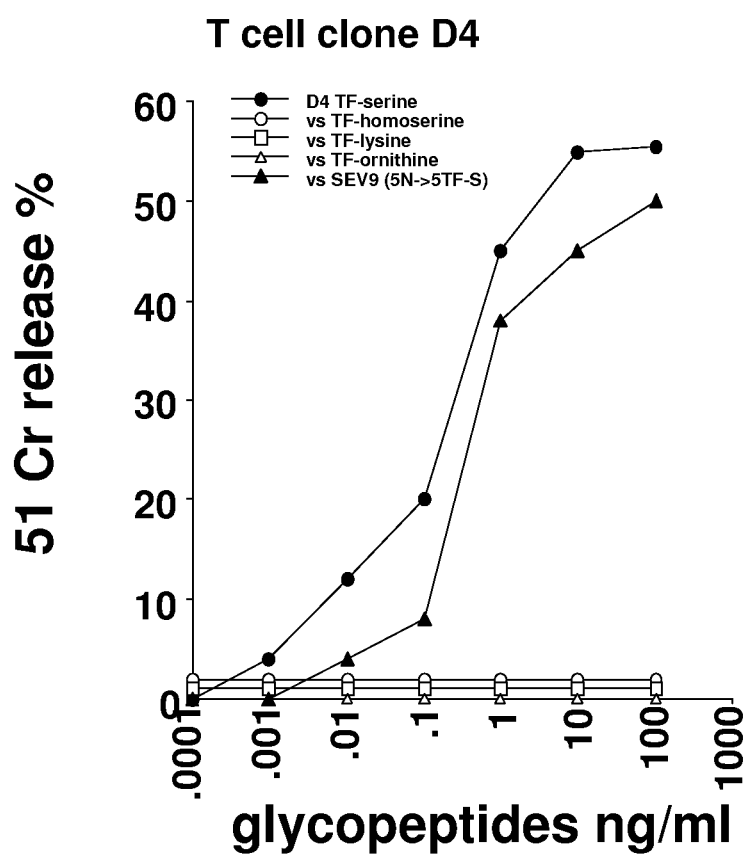

FIG. 1A (T cell clone B1), FIG. 1B (T cell clone C3) and FIG. 1C (T cell clone D4) illustrate the fine specificity and cross-reactivity of $\beta$-Gal-[1->3]-$\alpha$-GalNAc-O-specific T cell clones. The fine specificity of three representative $\beta$-Gal-[1->3]-$\alpha$-GalNAc-O-specific T cell clones was characterized by studying the cross-reactivity to a modified natural viral sequence from the Sendai virus carrying $\beta$-Gal-[1->3]-$\alpha$-GalNAc-O-linked to a serine in position 5, but with a completely unrelated peptide backbone sequence (FAPG($\beta$-Gal-[1->3]-$\alpha$-GalNAc-O-serine)YPAL) (filled triangles).

We also studied the cross-reactivity to glycopeptides with identical sequences as the immunogen, but carrying different amino acid linkers in position 5 for carbohydrate conjugation, as $\beta$-Gal-[1->3]-$\alpha$-GalNAc-O-homoserine, $\beta$-Gal-[1->3]-$\alpha$-GalNAc-O-lysine, and $\beta$-Gal-[1->3]-$\alpha$-GalNAc-O-ornithine (empty symbols). T cells were assayed at a 5:1 effector/target (E/T) ratio at different antigen doses. EL-4 cells (H-$2^b$) were used as target cells in these experiments (net lysis is shown, background lower than 2% for all the CTL clones studied). These clones did not respond to the peptide backbone AIIAS-FAAL, stressing the success of this exemplary vaccine of the invention in generating a TACA-specific CTL in vivo.

These findings demonstrate that $\beta$-Gal-[1->3]-$\alpha$-GalNAc-O-specific TcRs (on CTLs generated using exemplary compositions of this invention) recognize serine, the natural glycosylated amino acid linker in vivo, together with the sugar molecule.

MHC restriction and recognition of tumor targets by glycopeptide-specific CTL clones: The recognition of carbohydrate-expressing tumor targets (endogenous recognition) by CTL generated in vivo, immunizing with the invention's exemplary $\beta$-Gal-[1->3]-$\alpha$-GalNAc-O-S alanine-rich glycopeptide, validates the immunotherapeutic potential of TACA-based glycopeptides vaccines of this invention. Representative T cell clones, previously studied for cross-reactivity, were tested for their ability to recognize tumor cells that endogenously synthesize the carbohydrate antigen. The classic $^{51}$Cr release assay, 5:1 effector/target (E/T) ratio served as the read-out assay.

Three target tumor cell lines were selected in these experiments: 1) TA3/Ha, a well-characterized mammary carcinoma that expresses TF. TA3/Ha was transfected with a H-2K$^b$ plasmid (kindly donated by Dr Sebastian Joyce) to provide the appropriate syngeneic class I MHC allele for CTL recognition; 2) the MM14 ovary carcinoma (H-2$^a$) that expresses TF, which was also transfected with H-2K$^b$; and 3) the B16 melanoma cell line (H-2$^b$), transfected with the human MUC1 gene syngeneic with the T cell clones, designated as B16/MUC1. K$^b$ transfected carcinomas cell lines and B16/MUC1 express abundantly TF, as has been detected by FACS analysis using anti-TF monoclonal antibodies, kindly provided by Dr. Bo Jansson. The expression of TF on different tumor types has been published, see e.g., J. Exp. Med. 2004, 199:707.

Parental MM14 and TA3/Ha tumor cell lines (H-2$^a$) were used as mismatched controls for MHC restriction; the MUC1 negative melanoma B16 cell line (H-2$^b$) was used for carbohydrate specificity, respectively. EL-4 target cells (H-2$^b$), TF negative, were also assayed to determine the background that has been subtracted.

Figure 2A:
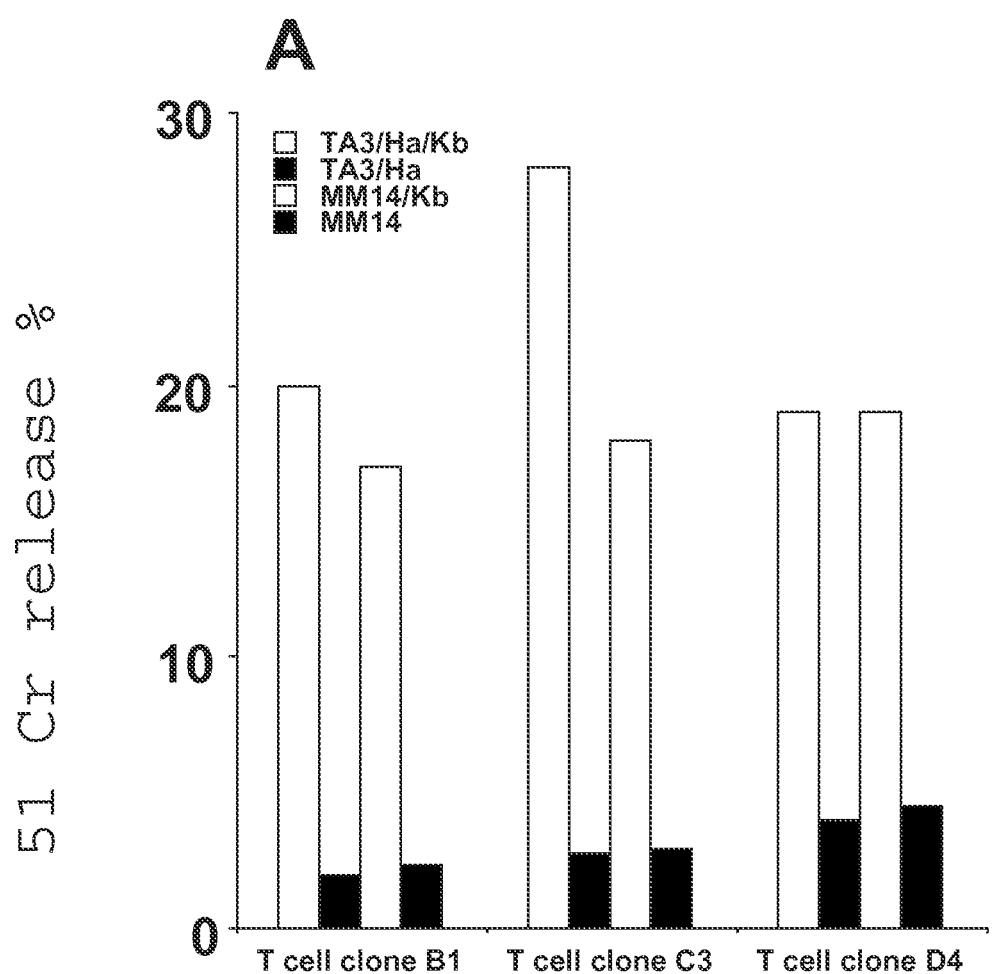
FIG. 2A and FIG. 2B illustrate endogenous TACA recognition and MHC restriction of β-Gal-[1->3]-α-GalNAc-O-specific T cell clones, as discussed in detail in Example 2, below.
Figure 2B:
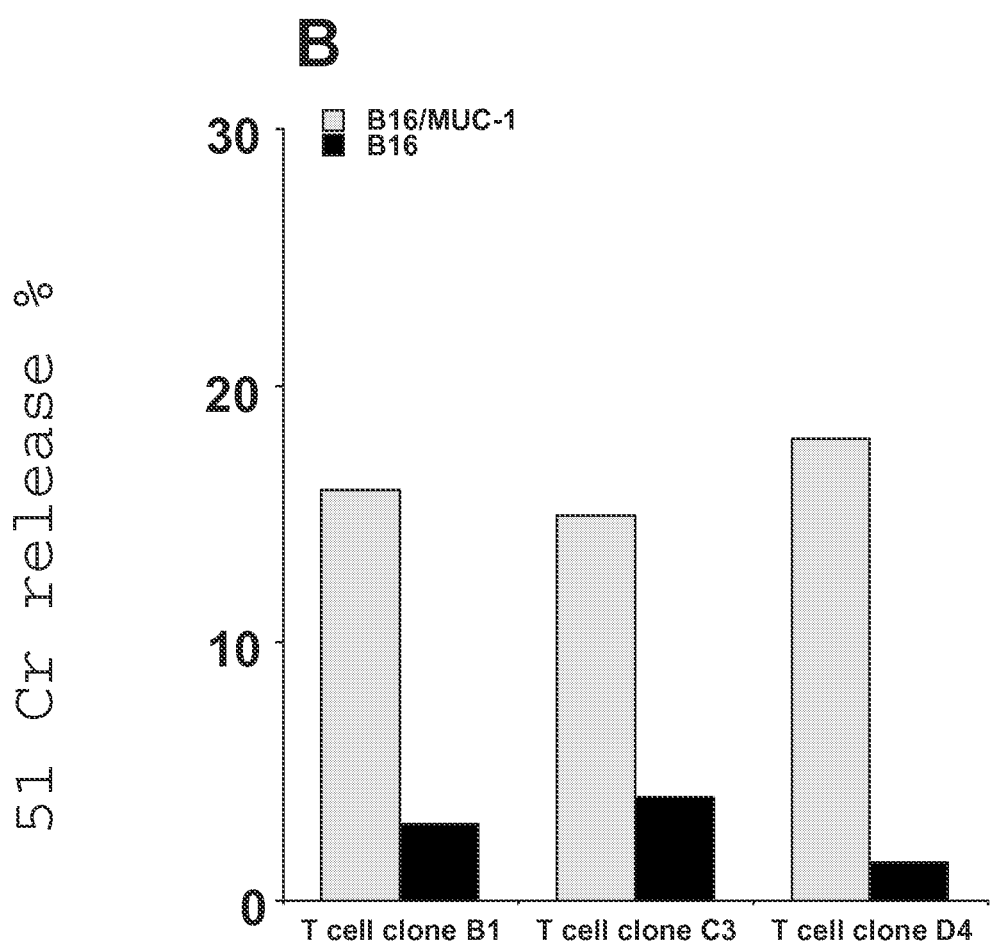

FIG. 2A and FIG. 2B illustrate endogenous TACA recognition and MHC restriction of β-Gal-[1->3]-α-GalNAc-O-specific T cell clones. Three representative β-Gal-[1->3]-α-GalNAc-O-S-specific T cell clones B1, C3 and D4, assayed at a 5:1 E/T ratio, recognize K$^b$-transfected mammary and ovary carcinomas that express β-Gal-[1->3]-α-GalNAc-O-S, but not the mismatched H-2$^a$ parental tumor lines, as illustrated in FIG. 2A.

B16 melanoma (H-2$^b$) transfected with the MUC1 gene, expressing β-Gal-[1->3]-α-GalNAc-O-S is also recognized by the same T cell clones, but not the parental melanoma B16 cell line lacking the β-Gal-[1->3]-α-GalNAc-O-S antigen (SD≤1.5 in three repeated experiments), as illustrated in FIG. 2B. High cytotoxic activity was observed against TA3/Ha/K$^b$ (mammary tumor) and MM14/K$^b$ (ovary tumor), but not against the parental H-2$^a$ tumor lines, which are mismatched for MHC class I molecules (H-2$^a$).

These findings indicate that β-Gal-[1->3]-α-GalNAc-O-S-specific CTL recognize the sugar antigen, which is endogenously expressed, in a classic MHC class I-dependent fashion (FIG. 2A). In support of the carbohydrate specificity, the same T cell clones were capable of killing the syngeneic melanoma cell line B16 (H-2$^b$) only when transfected with the MUC1 gene (B16/MUC1) containing β-Gal-[1->3]-α-GalNAc-O-S-, but were not capable of recognizing the MHC-matched parental B16 cell line, β-Gal-[1->3]-α-GalNAc-GalNAc-O-S-negative (FIG. 2B).

Glycopeptides of the invention designed to bind multiple class I MHC alleles in humans: Tn was chosen over TF in these studies because of its higher immunogenicity, probably due to the smaller size, which may imply a more stable conformation of the glycopeptides/class I MHC complexes, as suggested by previous studies, see, e.g., J. Exp. Med. 2004. 199:707. Moreover the fine specificity of TF-specific T cell clones suggested that Tn is the immunodominant carbohydrate molecule, see e.g., J. Exp. Med. 2004. 199:707.

We used either a natural serine or introduced serine substitutions for Tn-conjugation at a major TcR contact in peptide sequences already proven to have high affinity for A2 class I MHC molecules. Three of the peptides chosen for Tn conjugation were the well known and immunodominant CTL epitopes derived from the hepatitis B virus (HBV): HBV core 18-27; HBV polymerase (pol) 635-643 and 1447-1455. The other natural viral epitope chosen for glycosylation was HIV gp120, sequence 272-281, which is very relevant in the immune response to HIV and often mutated by immune pressure.

Each of these peptides contained a serine (S) corresponding to a major TcR contact in position 4 or 5, ideal for carbohydrate conjugation. As a proof of concept we also included a designer A2-binding alanine-rich peptide backbone, defined in Dr. Sette's laboratory, in this assay.

The affinity of GalNAc-modified sequences to A*0201 MHC molecules and some of its subtypes were compared to the binding of their corresponding native unmodified peptide.

The MHC binding assay was performed with purified MHC molecules. The A2 affinity of designer glycopeptides and corresponding peptide backbones is described in Table 1, below:

TABLE 1

The HLA binding capacity of A2 binding peptides and their glycopeptides variants

| Sequence | Virus | Protein | Position | Binding capacity (IC50) nmol/L | | | |
|---|---|---|---|---|---|---|---|
| | | | | A*0201 | A*0202 | A*0203 | A*0206 |
| FLP(GalNAc-O-S)DFFPSV | HBV | core | 18-27 | 0.19 | 2.6 | 0.31 | 1 |
| FLPSDFFPSV (SEQ ID NO: 18) | HBV | core | 18-27 | 1.3 | 53 | 8.6 | 0.95 |
| GLYS(GalNAc-O-S)TVPV | HBV | pol | 635-643 | 0.25 | 0.45 | 0.46 | 8.1 |
| GLYSSTVPV (SEQ ID NO: 19) | HBV | pol | 635-643 | 0.24 | 0.45 | 1.4 | 9.3 |
| FLL(GalNAc-O-S)LGIHL | HBV | pol | 1147-1155 | 1.4 | 6 | 42 | 3.8 |
| FLLSLGIHL (SEQ ID NO: 20) | HBV | pol | 1147-1155 | 8.9 | 9.7 | 519 | 16 |
| TLT(GalNAc-O-S)CNTSV | HIV-1 | gp120 | 272-281 | 0.72 | 15 | 8.2 | 24 |
| TLTSCNTSV (SEQ ID NO: 21) | HIV-1 | gp120 | 272-281 | 0.29 | 8.1 | 13 | 15 |
| ALA(GALNAc-O-S)SAAAAV | designer | — | — | 8.8 | 1.2 | 0.3 | 81 |
| ALASAAAAV (SEQ ID NO: 22) | | — | — | 114 | 36 | 21 | 266 |

For Table 1:
FLPSDFFPSV is SEQ ID NO: 18
GLYSSTVPV is SEQ ID NO: 19
FLLSLGIHL is SEQ ID NO: 20
TLTSCNTSV is SEQ ID NO: 21
ALASAAAAV is SEQ ID NO: 22

Native peptide epitopes were confirmed to be good A*0201 binders. The GalNAc-O-S containing glycopeptide variants also bound with very good affinity, sometimes even better than the wild-type peptides (Table 1). The capacity of glycopeptides to bind different A2 subtypes was also retained, demonstrating that the vaccines of this invention can target a large population of tumor types covering different class I HLA alleles. These observations justified the use of designer glycopeptides in functional experiments to evaluate their immunogenicity and also indicated that glycopeptides of this invention can generate strong and sustained anti-Tn CTL responses in vivo.

HBV- and HIV-derived glycopeptides prime with high efficiency naïve CD8+ T cells healthy A2 donors: Three out of five glycopeptides and peptides described in Table 1 (see above) were studied for their ability to prime in vitro naïve cytotoxic T cells derived from peripheral blood mononuclear cells (PBMC) of normal donors.

Seven A2+ healthy individuals, never exposed to HBV or HIV, between ages 40 and 57, were included in the study. Autologous, antigen-pulsed, mature dendritic cells (DC) were used as antigen presenting cells (APCs) for the in vitro priming. Autologous DC were cultured with granulocyte/macrophage colony stimulating factor (GM-CSF) (kindly provided by Kirin, Japan) and interleukin (IL) 4 (Peprotech, Rocky Hill, N.J.).

Twelve (12) independent CTL lines with glycopeptide specificity and 12 CTL lines with peptide specificity were established by co-culturing in 48 wells flat-bottom plates $5 \times 10^5$ fresh PBMC/well and $1 \times 10^5$ mature DC/well. DC were previously pulsed for 2 hours with glycopeptides(s) or peptide(s). Each well defined an individual CTL line.

FACS analysis indicated that CD8+ T cells represented an average of 25% of the total PBMC, ranging from 13% to 37% in different donors prior to cultures. By using the culture conditions and IL2 regimen optimized over several years in our laboratory, the large majority of the PBMC in culture are T cells at day 10. CD8+ T cells represent the majority. The initial calculation renders possible an approximation of the precursor frequency of the CTL newly primed in vitro.

T cell cultures were tested for specificity at day 10 in a $^{51}$Cr release assay. T2 cells (A2) were used as targets at 3:1 E/T ratio. T cell lines primed in vitro with glycopeptides were tested for the ability to recognize T2 cells pulsed with the glycopeptides, or the peptide backbones, or to untreated T2 cells (background control). Peptide-primed T cell lines were also tested for their ability to respond to peptides and cross-react with the corresponding GalNAc-O-S modified sequence.

The results obtained in vitro in these experiments are summarized in Table 2, below. CTL lines showing a net specific lysis ≥20% were considered specific. Carbohydrate recognition was defined as a specific response to the glycopeptides, after subtracting the background and the specific response to the corresponding peptide backbone.

TABLE 2

Immunogenicity of Tn-containing glycopeptides compared to natural un-glycosylated sequences

| | Donor 1 | Donor 2 | Donor 3 | Donor 4 | Donor 5 | Donor 6 | Donor 7 | Total |
|---|---|---|---|---|---|---|---|---|
| FLP(GalNAc-O-S)DFFPSV | 5 | 5 | 1 | 3 | 4 | 2 | 4 | 24 |
| FLPSDFFPSV (SEQ ID NO: 18) | 1 | 1 | 3 | 6 | 3 | 2 | 4 | 20 |
| GLYS(GalNAc-O-S)TVPV | 6 | 2 | 1 | 1 | 4 | 4 | 2 | 20 |
| GLYSSTVPV (SEQ ID NO: 19) | 2 | 0 | 1 | 3 | 5 | 2 | 2 | 15 |
| TLT(GalNAc-O-S)CNTSV | 7 | 4 | 0 | 1 | 5 | 1 | 5 | 23 |
| TLTSCNTSV (SEQ ID NO: 21) | 1 | 0 | 0 | 7 | 3 | 5 | 2 | 18 |

PBMC from normal donors have been stimulated in vitro with either glycopeptides or corresponding peptide sequences. The number of specific CTL lines out of the 12 obtained from individual donors is shown.

A large number of glycopeptide-specific and peptide-specific CTL lines were generated following a single stimulation with the antigens—compositions of the invention—in the 7 donors studied. The unmodified peptides tested were immunogenic in this in vitro system, as expected and previously reported.

However, glycopeptides of the invention were even more immunogenic than their corresponding native peptides, as indicated by the total number of specific CTL lines generated in vitro with GalNAc-O-S modified sequences compared to corresponding native peptides (Table 2, right column).

Next we synthesized a variety of tumor-related glycopeptides by studying the MUC1 glycoprotein highly expressed in carcinomas as a product of aberrant glycosylation.

Identification of vaccine epitopes candidates: In one embodiment, small carbohydrate antigens within the MUC1 carbohydrate are used in a composition of this invention as an antigen for immunotherapy in, e.g., carcinomas; these exemplary glycopeptides were tested in a variety of formulations involving MUC1-derived peptide epitopes in clinical trials. This invention the first time uses small carbohydrate antigens within the MUC1 glycoprotein as a therapeutic, e.g., "designer", glycopeptide.

The identification of candidate vaccine epitopes from the three Tn-containing glycopeptides proceeded in three steps: 1) computer analysis of the primary protein sequence to identify peptides with a high likelihood of binding HLA-A2 super-type molecules; 2) direct measurement of MHC binding affinity of the peptides to A2 supertype receptors (a variety of A2 alleles); and 3) immunogenicity testing of high affinity MHC-binding peptides for cytotoxic T cell induction.

We designed a variety of MUC1-derived glycopeptides on the basis of those parameters and our results show successful for TcR recognition of Tn conjugation in a central position within the peptide backbone.

In alternative embodiments, small carbohydrate antigens within the MUC1 carbohydrate are used in a composition of this invention; MUC1 is an excellent glycoprotein target for T cell-based immunotherapy. While the invention is not limited by any particular mechanism of action, since the MUC1 molecule is heavily glycosylated, where Tn is a carbohydrate largely represented, the success of a vaccine may depend on addressing carbohydrate T cell recognition.

Table 3 below shows the binding data of a variety of exemplary Tn-containing glycopeptides of this invention that allowed the selection of the best 3 candidates for a Phase 1 clinical trial.

TABLE 3

Designer MUC1-derived glycopeptides chosen for in vitro and in vivo studies (Tn in positions 4-6)

| Sequences** | Protein sources | Glycopeptides | A*0201 $K_D$ nM* | A*0202 $K_D$ nM* | A*0203 $K_D$ nM* |
|---|---|---|---|---|---|
| ALGSTAPPV (SEQ ID NO: 4) | MUC1 167-175 | ALG(Tn-S)TAPPV | 24 | 51 | 154 |
| LLLLTVLTV (SEQ ID NO: 23) | MUC1 signal sequence | LLLL(Tn-T)LTV | 1303 | >8000 | 4287 |
| FLPDTRFAV (SEQ ID NO: 24) | Designer/MUC1 core repeat | FLPD(Tn-T)RFAV | 638 | 194 | 114 |
| FLPDTRFYV (SEQ ID NO: 25) | Designer/MUC1 core repeat | FLPD(Tn-T)RFYV | 45 | 18 | 60 |
| FLFPDTRAV (SEQ ID NO: 26) | Designer/MUC1 core repeat | FLFPD(Tn-T)RAV | 43 | 1.4 | 5.6 |
| FLFPDTRYV (SEQ ID NO: 27) | Designer/MUC1 core repeat | FLFPD(Tn-T)RYV | 21 | 1.5 | 6.1 |

*MHC binding capacity was measured as the quantity of peptides required that inhibit by 50% the binding of a well-characterized radioiodinated binding peptide.
**The amino acid residues selected for O-glycosylation are bold and underlined.

We selected for a Phase 1 trial 3 A2-restricted exemplary "designer" glycopeptides of the invention containing the MUC1 PDTR motif (4, 5, 6 in Table 3) on the basis of their ability to bind a variety of A2 subtypes, representing supertype motifs and therefore useful in a large population.

Glycopeptides can break immunological tolerance in tumor bearing mice (MUC1/MT): In one aspect, the invention provides glycopeptides comprising carbohydrate moieties having abnormal, or "non-self", epitopes because cancer patients can be tolerant to vaccines that contain tumor epitopes that are "self" or embryonic antigens. Thus, in one aspect, the invention provides vaccines able to break immunological tolerance.

Here we address the capacity of glycopeptides to induce anti-TACA CTL in mice that develop spontaneous mammary tumors. These mice, named MUC1/MT, were exposed in the embryo to TF and Tn TACA antigens.

In repeated experiments we searched TF- and Tn-specific CTL in the spleen of unprimed mice without success, proving T cell tolerance to the TACA antigens.

The glycopeptides-based vaccination in MUC1/MT transgenic mice have been carried out with the Tn-containing alanine-rich glycopeptide AIIA(GalNAc-O-S)FAAL (note AIIASFAAL is SEQ ID NO:28), previously described as highly immunogenic. In these experiments, MUC1/MT mice have been chosen according to age and tumor development.

Two female mice/group (14, 18, and 24 weeks old) were immunized with the glycopeptide emulsified in incomplete Freund's adjuvant (IFA) in repeated experiments. Seven days after priming, mice were sacrificed. Splenocytes from each experimental group were pooled and stimulated in vitro in the presence of the glycopeptide that was used as immunogen and irradiated B cell blasts as antigen presenting cells (APCs). After 5 days in culture, cells were collected, purified over Ficoll gradient, and T cell blasts were cultured in complete RPMI conditioned with supernatant from ConA-activated splenocytes as an IL2 source. Two days later (day 7 in culture) T cells were tested for CTL activity.

Carbohydrate and peptide specificity were studied in a standard $^{51}$Cr release assay using the lymphoma EL-4 (H-$2^b$) cell line as target at different effector: target ratios (E/T) in duplicate, with and without antigens. Carbohydrate specificity was investigated by comparing the response between the glycopeptide and its respective non-glycosylated counterpart. Net specific lysis has been calculated by subtracting the cytolytic response to EL-4 cells alone without antigens defined as background. Data were calculated as % cytotoxicity=[(sample-spontaneous release)/(maximum release-spontaneous release)]×100. Strong CTL activity in response to the immunizing glycopeptide was generated in MUC1/MT transgenic mice, regardless of their age and tumor progression; as illustrated in FIG. 3.

In contrast, greatly diminished activity was observed against the same peptide in the non-glycosylated form (particularly evident at lower E/T ratios), demonstrating the generation of Tn-specific CTL that either do not use T cell receptor (TcR) contacts within the peptide backbone or are not activated if such contacts exist, as previously shown in wild type mice. As controls, an equal number of wild type C57BL/6 female mice where immunized side-by-side with the same Tn-containing glycopeptide in these experiments, proving that Tn-specific CTL responses in intact mice are absolutely comparable to the one obtained in the double transgenic MUC1/MT.

Figure 3:
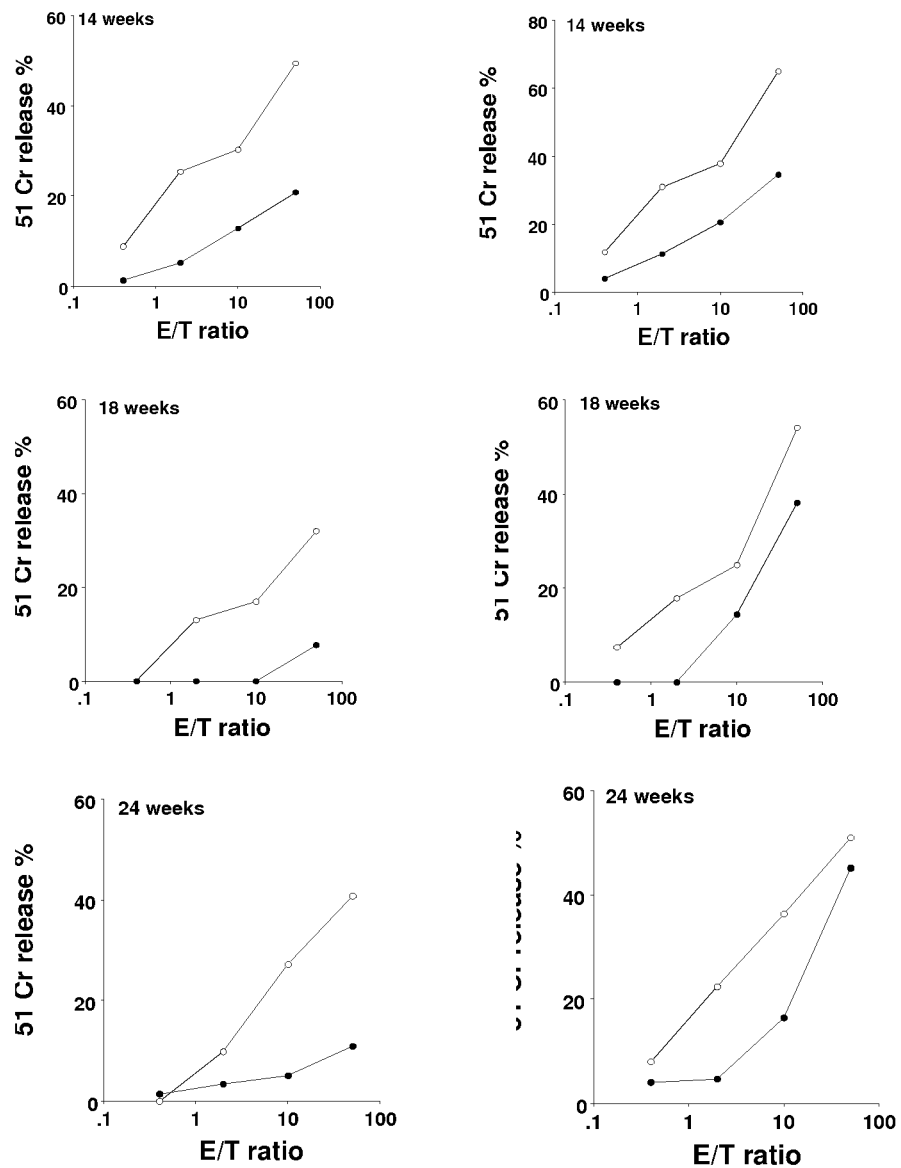
FIG. 3 illustrates CTL response to a Tn-containing glycopeptide vaccine in MUC1/MT mice, as discussed in detail in Example 2, below.

FIG. 3 illustrates CTL response to a Tn-containing glycopeptide vaccine in MUC1/MT mice. Specificity of primary CTL cultures tested in a $^{51}$Cr release assay is shown. Labeled EL-4 cells (H-$2^b$) were incubated with different cell number of T cell blasts in the presence of 1 μg/ml of AIIA(GalNAc-O-S)FAAL (empty symbols) or AIIASFAAL (SEQ ID NO:28) (full symbols). EL-4 cells plated with T cell blasts in the absence of antigens have been assessed in duplicate at every E/T ratio to determine the extent of non-specific lysis. Cell cultures supernatants were harvested four hours later and percent $^{51}$Cr released was calculated as (sample-spontaneous release)/(maximum release-spontaneous release)×100. Background lysis has been subtracted and net lysis is shown. A representative experiment where two mice aged 14, 18 and 24 weeks is shown. Mice were carrying tumors of different sizes, according to their age.

Vaccine design administration: In this embodiment, the final vaccine product comprises a cocktail of three (3) exemplary cytotoxic T cell-inducing synthetic glycopeptides of the invention; the peptides can be emulsified and delivered in an adjuvant, e.g., MONTANIDE ISA 51®, a mannide oleate-based mineral oil adjuvant with a documented history of low toxicity in humans. Due to its confirmed safety profile, MONTANIDE ISA 51® has commonly been used in several clinical trials to augment antibody and T cell responses against peptide and protein antigens.

In this embodiment, the vaccine of the invention comprises a glycopeptide cocktail vaccine formulated to be injected subcutaneously into patients at alternating sites in a volume not to exceed 1 ml total per treatment dose. Prostate cancer patients can receive a single dose of peptide cocktail vaccine with each patient receiving 0.5 mg of each glycopeptide; e.g., about 1.5 mg total dose per treatment. Immunization frequency can be every 4 weeks, e.g., for a total of 3 injections.

Proposed Preclinical safety studies: To date no studies designed to assess preclinical safety have been conducted. Multiple single dose in vivo experiments in wild type C57BL/6 mice and MUC1/MT double transgenic mice (that develop spontaneous mammary tumors within 12 weeks of age) have been performed without any evidence of significant local irritation at injection sites, morbidity or mortality (starting 10 days up to 3 months post-treatment observation period). Each individual peptide has been administered to at least in six (6) wild type and three (3) double transgenic mice at a dose level of 0.07 mg/kg. The 3-glycopeptide pool has been administered to six (6) wild type C57BL/6 mice at 0.21 mg/kg total glycopeptides pool, 0.07 mg/kg per individual glycopeptide.

Mice were healthy, with shiny fur and no CNS or pulmonary symptoms observed up to 4 months after glycopeptides administration. Autopsied wild type mice did not show any liver, lung, spleen or brain abnormalities. It is worth noticing that the spleen was not enlarged although it represents the major source of CD8+ T cells in rodents. These results prove that only specific T cell clones (pre-selected in the thymus in pre-natal life) have been activated with this exemplary vaccination protocol of this invention. In these experiments, the glycopeptides individually or as the three (3) glycopeptide pool were formulated with the same incomplete adjuvant, and administered subcutaneously, as intended for the clinical Phase 1 studies.

In one embodiment, the invention provides a glycopeptide vaccine, e.g., a TF- or Tn-containing glycopeptide vaccine, as a sterile formulation of one or more glycopeptides of this invention, e.g., the three (3) individual glycopeptides/epitopes pooled in a formulation, e.g., an aqueous/DMSO buffer system and emulsified with an adjuvant, e.g., an incomplete Freund's adjuvant (e.g., MONTANIDE ISA 51®, Seppic Inc.); final glycopeptide concentrations in the vaccine can be about 0.5 mg/ml for each glycopeptide, or about 1.5 mg/ml for total glycopeptides pool. The control formulation will be the aqueous/DMSO buffer system only emulsified with the adjuvant, e.g., MONTANIDE ISA 51®.

In alternative embodiments, glycopeptides of the invention are administered via subcutaneous or intradermal injection; all preclinical safety studies are conducted using the pool of three glycopeptides, formulated with processes equivalent to those used for the manufacture of clinical supplies; the manufacturing scale of glycopeptides for preclinical safety studies can be 5 fold the dose to be used in humans (5 mg each individual glycopeptide, 15 mg the glycopeptides pool).

Glycopeptides for the safety studies can be filled into Teflon—coated rubber stoppered vials vs the pre-filled syringe product to be used for clinical supplies. Glycopeptides can be formulated to the highest peptide concentrations possible based on the individual glycopeptide solubilities in the manufacturing process solvents. The highest allowable concentration can be what will be used for the clinical supplies. Dose adjustments for the safety studies can be accomplished by altering injection volumes. An exemplary preclinical safety treatment schedule and dosage is:

| Preclinical Studies 5 Rx | Dose Exposure per Treatment | | | Total Dose Exposure | | |
|---|---|---|---|---|---|---|
| 3 administrations: 0, 4, 8 wks | Total Mg | Mg/Kg | Mg/M$^2$ | Total mg | Mg/Kg | Mg/M$^2$ |
| One Dose | 7.5 | 0.07 | 1.75 | 22.5 | 0.21 | 5.25 |

Dose exposure per treatment = The total mg of glycopeptides administered per treatment
Total Dose Exposure = The total mg of glycopeptides administered over the study period
Mg/M$^2$ = milligrams peptide per square meter of body surface area
Mg/Kg = milligrams peptide per kilograms total body weight In one embodiment, for dose selection—because glycopeptides with high affinity for class I MHC molecules are used in exemplary glycopeptides of this invention, and because they are very immunogenic in vivo at very low doses in mice (e.g., about 1 µg/mouse); exemplary dosages used to practice this invention comprise use of about 0.5 mg/each (per) glycopeptide of the invention; with in alternative embodiments a total of about 1.5 to 2 mg within an exemplary pool; these dosages are efficient in generating a robust cytotoxic T cell response in vivo. A higher dose may have an inhibitory effect by inducing T cell tolerance.

In one embodiment, a composition, e.g., vaccine, of the invention comprises one, two or three or more individually synthesized glycopeptides of the invention. In one embodiment, glycopeptides are designed to comprise the "PDTR" repeated core of the MUC1 glycoprotein and major A2 anchors to optimize binding.

In one embodiment, glycopeptides of the invention comprise a tumor associated carbohydrate antigen Tn (α-GalNAc) in position 4-6, which can be ideal for T cell receptor recognition:

1. FLPD(GalNAc-T)RFYV  (FLPDTRFYV is SEQ ID NO: 25)

2. FLFPD(GalNAc-T)RAV  (FLFPDTRAV is SEQ ID NO: 2)

3. FLFD(GalNAc-T)RYV  (FLFDTRYV is SEQ ID NO: 28)

In one embodiment, glycopeptides of the invention are synthesized by "parallel synthesis" of the glycopeptides by the solid phase methodology, e.g., starting from methylbenzhydrylamine resin. Assemblies of glycopeptides can be performed in parallel using tea-bag technology. The building block containing the protected saccharide attached to an amino acid side chain can be used directly in the solid-phase synthesis of the glycopeptide. Serine, threonine and tyrosine can be protected on their side chain functions as tert-butyl ethers. Pmc will be used as the guanidino protective group for arginine and the ε-amino function of lysine will be masked as the Boc derivative. Standard solid phase peptide Fmoc strategy using HBTU/HOBt/DIEA can be used. Coupling completion can be monitored by ninhydrin analysis. Removal of the side chain protecting groups and cleavage from the resin can be done simultaneously by treatment with TFA and scavengers. The acid solutions can be concentrated to small volumes and the desired peptides and glycopeptides can be precipitated by the addition of cold tert-butyl ether. The resulting precipitates can be collected and dried in vacuo. Deacylation of the carbohydrate moieties can be achieved by adding hydrazine hydrate to a concentrated methanolic solution of the crude glycopeptide (or by using a dilute solution of NaOH). All synthesized peptides and glycopeptides can be purified by e.g., semi-preparative reversed phase-high performance liquid chromatography (RP-HPLC) and further characterized and analyzed by mass spectral analysis interfaced with a liquid chromatography system (Finnigan LCQ) and analytical RP-HPLC using a Beckman System Gold HPLC.

Figure 4:
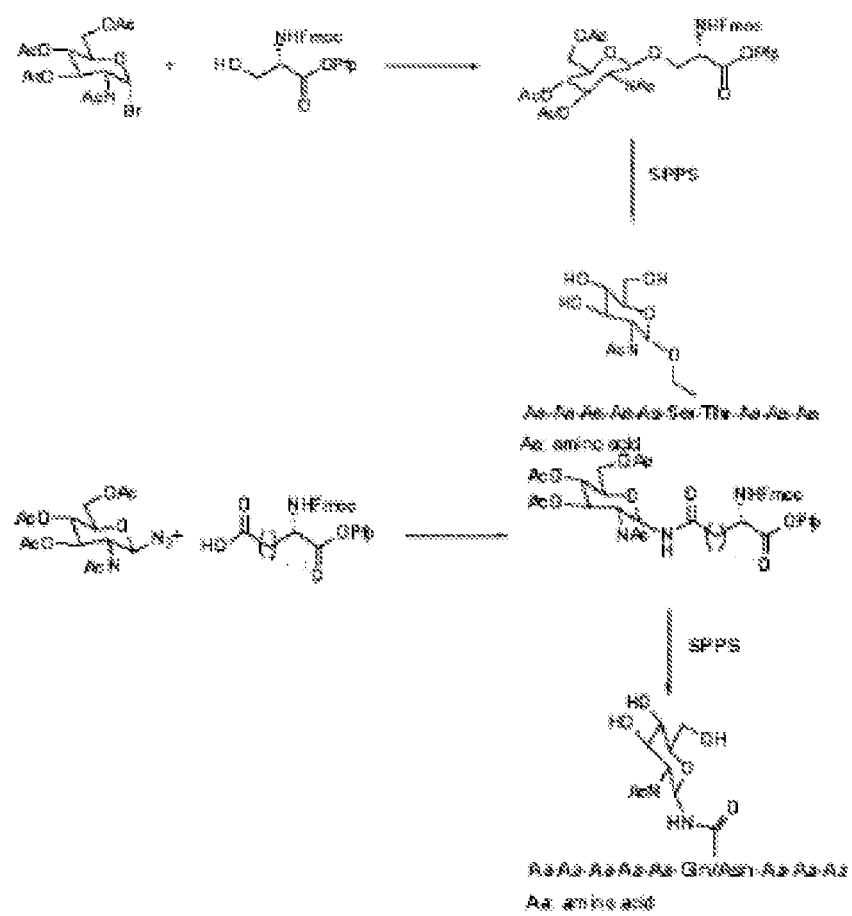
FIG. 4 illustrates two exemplary schemes for the synthesis of glycopeptides of this invention, including glycopeptides comprising an -O-glycosylated serine and threonine derivatives containing a peracetylated monosaccharide unit, and glycopeptides comprising N-glycosylated asparagine and glutamine derivatives, as discussed in detail in Example 2, below.

In one embodiment, -O-glycosylated serine and threonine derivatives containing a peracetylated monosaccharide unit are synthesized, as shown in FIG. 4, upper half of the figure. In one embodiment, the synthesis of N-glycosylated asparagine and glutamine derivatives is achieved as shown in FIG. 4, lower half of the figure. FIG. 4 illustrates two exemplary schemes for the synthesis of glycopeptides of this invention, including glycopeptides comprising an -O-glycosylated serine and threonine derivatives containing a peracetylated monosaccharide unit, and glycopeptides comprising N-glycosylated asparagine and glutamine derivatives.

Solubility of the Individual Peptides: Glycopeptides of the invention can be soluble when diluted in Dimethylsulfoxide (DMSO); and the three epitopes FLPD(GalNAc-T)RFYV (FLPDTRFYV is SEQ ID NO:25); FLFPD(GalNAc-T)RAV (FLFPDTRAV is SEQ ID NO:2) and FLFD(GalNAc-T)RYV (FLFDTRYV is SEQ ID NO:28) are all very soluble when diluted in Dimethylsulfoxide (DMSO). Solubility is defined as a clear solution with no visible particulates.

Preparation of Glycopeptides Solution (Dimethylsulfoxide Pool): in One Embodiment, glycopeptides are dissolved in dimethylsulfoxide, e.g., in a solution comprising or consisting of glycopeptides dissolved in dimethylsulfoxide at 25 mg/mL. The glycopeptide are dissolved by gentle stirring at ≤37° C. The solution is then sterilized by filtration through a 0.2μ nylon filter into an appropriate sterile container. The resulting sterile solution is stored at about 2° C. to 8° C. until preparation. Limited stability studies indicated that this pool is stable for at least 72 hours when stored at 2° C. to 8° C. An in-process test can be performed to confirm the concentration of the peptide.

Preparation of glycopeptides pool (e.g., a combined pool of all three exemplary glycopeptides): Glycopeptides pool (combined pool) is prepared under aseptic conditions. A final glycopeptide concentration can be obtained in aseptic conditions by the addition of 70 gm of sterile 0.5 N sodium hydroxide. To buffer the solution 86 mL of 0.0625 M phosphate, pH 7.0 buffer is added. Water for injection is then added to adjust the solution to the desired concentration. The solution is then stirred for approximately 1 hour. The resultant sterile solution is a cloudy mixture of the 3 glycopeptides that is stable for at least 72 hours.

Preparation of drug product: In one embodiment, glycopeptides are prepared as a stable emulsion. A sterile stable emulsion can be prepared by homogenization under aseptic conditions of a 1:1 (w:w) mixture of a glycopeptides pool (a mixture of two or more glycopeptides of this invention) and MONTANIDE ISA 51® using a Silverson L4RT™ homogenizer (Silverson Machines, Inc. East Longmeadow, Mass.) fitted with the appropriately sized probe. For example to prepare 1 L of emulsion, 460 mL of MONTANIDE ISA 51® is added to a sterile container and the probe of the Silverson homogenizer is started in the oil at a slow (1000 rpm) speed. While the oil is agitating, the final concentration of the glycopeptides pool is added over one minute. The homogenization speed is increased to 7000 rpm and mixing continued for approximately 15 minutes.

Specification of Drug Product

| Test Name | Test Method | Specification |
|---|---|---|
| Appearance | Visual | Viscous white emulsion |
| Endotoxin | USP 24 <85> | ≤5 EU/mL |
| Sterility | 21CFR600 | No growth after 14 days |
| Viscosity | | Report value |
| Peptide concentration of each glycopeptide | HPLC | 0.5 mg/mL ± 0.1 mg/mL |

Potency assay: In alternative embodiments, pools of glycopeptides of the invention (e.g., the pool of three Tn-containing glycopeptides described in this example) are composed (comprised) of totally synthetic cytotoxic T cell epitopes whose content and integrity can be accurately determined by e.g., physical/chemical characterization using any analytical method, e.g., the analytical methods described herein.

In alternative embodiments, the glycopeptides vaccines of this invention are designed to specifically stimulate HLA-restricted cytotoxic T cell responses in animals or humans, following e.g., one or more subcutaneous injections. As earlier explained, A2/$K^b$ transgenic mice and MUC1/MT/A2/$K^b$ triple transgenic mice are not appropriate to test (human) A2-restricted glycopeptides in vivo because although they respond vigorously to glycopeptides vaccines, their T cell repertoire has a broad cross-reactivity to the peptide backbones. This is probably due to the interference of Tn (sugar molecule) binding with some major or minor murine MHC alleles.

In one embodiment, a standardized in vitro priming of peripheral blood mononuclear cells (PBMC) derived from healthy A2 donors by using autologous dendritic cells (DC) as antigen presenting cells for cytotoxic T cell priming is used e.g., to evaluate and/or standardize the potency of any particular glycopeptide or glycopeptide combination of the invention, or formulation of the invention (e.g., to evaluate the composition of a formulation or dosage of glycopeptides of the formulation).

Epitope competition does not occur when the pool of three glycopeptides have been used as immunogen in vitro, as has been defined by measuring cytotoxic T cell responses to individual glycopeptides in cytotoxic T cell cultures established with autologous DC pulsed with all three glycopeptides epitopes in the vaccine.

In one embodiment, the invention provides compositions (e.g., therapeutic vaccines) and methods to treat individuals with cancer, e.g., patients with prostate cancer, with one glycopeptide or a glycopeptide combination ("a pool") of the invention, e.g., with a pool of the described three (3) A2-restricted Tn-containing glycopeptides as a therapeutic vaccine. In alternative embodiments, therapeutic vaccines of this invention are used to ameliorate, treat and/or prevent cancers, or to ameliorate, treat and/or prevent metastasis. In one embodiment, therapeutic vaccines of the invention use (comprise) the carbohydrate Tn, which can be an excellent target for cytotoxic T cell-based immunotherapy because: 1) Tn is early expressed in prostate cancer (and many others carcinomas) as a product of aberrant glycosylation; 2) Tn and the disaccharide TF (that contains Tn) represent a critical tool for invasiveness through metastasis.

In alternative embodiments, therapeutic vaccines of this invention comprise glycopeptides designed to bind with very high affinity a variety of subtypes of the A2 human class I HLA molecule(s), representing a proof of concept that a single antigenic target may be successfully used in a large population. In aspect, therapeutic vaccines of this invention are used to ameliorate, treat and/or prevent cancer of epithelial origin, e.g., prostate cancers, or to ameliorate, treat and/or prevent metastasis in prostate cancer patients.

In one aspect, glycopeptides are emulsified, e.g., in an adjuvant, e.g., in CFA or IFA, or MONTANIDE ISA 51®, Seppic Inc., or any adjuvant equivalent to an incomplete Freund's adjuvant (IFA). In one aspect, vaccines of this invention generate primary and memory anti-Tn CTL responses; and can lower PSA serum levels.

In one embodiment, a patient population appropriate for receiving administration of a vaccine of this invention is:
1. HLA A2+
2. Aged 50-80 years.
3. Diagnosed with biopsy-proven adenocarcinoma of the prostate within the prior 48 months.
4. Completed primary therapy with intent to cure with prostatectomy, brachytherapy or external beam radiation.
5. ≥18 months life expectancy.
6. Prostate serum antigen (PSA) of at least 0.3 ng/ml
7. PSA since reaching 0.3 ng/ml documented to have doubling time >9 months by 3 successive readings at least 3 months apart.
6. Subjects with prostate cancer must have had a CT scan of the abdomen and pelvis within 84 days (12 weeks) prior to enrollment.
7. Subjects with prostate cancer will have had a negative bone scan within 112 days (16 weeks) prior to enrollment.
8. Patients with prostate cancer treated with non-steroidal anti-androgens (flutamide, bicalutamide, nilutamide or ketoconazole) must stop these drugs at least 28 days prior to enrollment for flutamide or ketoconazole and at least 42 days prior to enrollment for bicalutamide or nilutamide with subsequent demonstrated progression.
9. Subjects may have received prior surgery. However, at least 21 days must have elapsed since completion of surgery and subjects must have recovered from all side effects.
10. Subjects must have recovered from major infections and/or surgical procedures and, in the opinion of the investigator, not have any significant active concurrent medical illness precluding safe protocol treatment or 6 month survival.
11. Subjects must meet the following initial laboratory criteria: granulocytes ≥1500/ml; platelet count ≥100,000/ml; hemoglobin ≥11 gms/dl; bilirubin ≤1.5×ULN; AST ≤1.5×ULN; Creatinine ≤1.5×ULN.

In some aspects, the clinical may want to consider certain exclusion criteria, such as:
1. ECOG Performance status >2.
2. Chemotherapy or radiation therapies within the past 30 days from the beginning of the study. Prior vaccine therapy is not allowed. Subjects who have received prior therapy must have demonstrated progression after completion of this therapy prior to enrollment.
3. Subjects receiving biphosphonate therapy prior to treatment must have received biphosphonates for more than 28 days prior to enrollment.
4. Immunosuppressive therapy in the past 30 days, including corticosteroids at greater than replacement doses. Replacement doses of corticosteroids are allowed in subjects with adrenal insufficiency. No other chemotherapeutic, biologic response modifier, radiation therapy, corticosteroid, or hormonal therapy (other than continuing LHRH treatment) may be given during protocol treatment.
5. Patients with prior malignancy are excluded if, in the judgment of the principal investigator, the prior diagnosis might reasonably interfere with the safe conduct of and/or analysis of the effect of the vaccine.

During the course of treatment, e.g., to determine the appropriate vaccination regimen and/or dosage of glycopeptides of the invention to be administered (e.g., as in a vaccine formulation), blood samples can be collected and used to measure antigen-specific CTL expansion and PSA levels, e.g., Tn-specific CTL expansion and PSA levels. To measure the primary Tn-specific CTL expansion after 1 vaccine dose, a blood sample (50 ml) can be collected at week 4, prior to the second vaccination.

During the course of treatment, e.g., to determine the appropriate vaccination regimen and/or dosage of glycopeptides of the invention to be administered (e.g., as in a vaccine formulation), CTL or helper T cell memory can be measured; for example, in one embodiment, to measure CTL or helper T cell memory, a third blood sample (50 ml) can be collected at week 16, a month after the third and last vaccine boost. PSA levels also can be monitored from the same blood samples. Safety can be assessed by changes from baseline in the following parameters: physical and ophthalmologic examinations findings, vital sign measurements, clinical laboratory test results, and performance scores. The incidence, severity and causal relationship of adverse events to the study drug can be evaluated. Serious adverse events, study discontinuations due to study drug, and deaths will be summarized.

During the course of treatment, e.g., to determine the appropriate vaccination regimen and/or dosage of glycopeptides of the invention to be administered (e.g., as in a vaccine formulation), immunogenicity studies can be used. For example, in one aspect, the size of a primary and/or memory Tn-specific CTL or helper T cell response to the administered vaccine, e.g., a glycopeptide pool and/or to individual glycopeptides of the invention, can be measured; for example:

Measurement of the primary CTL expansion: In one embodiment, during the course of treatment, e.g., to determine the appropriate vaccination regimen and/or dosage of glycopeptides of the invention to be administered (e.g., as in a vaccine formulation), CTL responses to individual glycopeptides will be investigated; e.g., at week 4, prior to the second glycopeptide-pool vaccine administration, CTL responses to individual glycopeptides are investigated.

In alternative embodiments, two different assays are used for this analysis: 1) ex vivo measurement of IFN-γ production by intracellular staining in the context of glycopeptide(s)/A2 tetramers for single-cell FACS staining; and 2) measurement of cytolytic activity after culturing, e.g., measuring cytolytic activity of the Tn-specific cytolytic activity after culturing.

Glycopeptides/A2 tetramers can be purchased at Beckman Coulter Immunomics, San Francisco, Calif. The tetramer analysis can be performed with individual glycopeptides as described herein. Ranking of in vivo immunogenicity of individual epitopes possible epitope-competition can be helpful.

Prior to FACS analysis CD8+ T cells can be enriched by negative selection, using antibodies coated to magnetic beads. Results can be calculated as the percent (%) of tetramer positive T cells that produce IFN-γ in response to individual glycopeptides, calculated over 1×10⁶ CD8+ T cell blasts. The $^{51}$Cr release can be also performed after stimulating CD8+ T cells for 7 days in culture to measure the cytolytic response to glycopeptides and to A2+ Tn-expressing tumors at different E/T ratios. The results can be quantified in LU.

Measurement of CTL Memory:

In one embodiment, during the course of treatment, e.g., to determine the appropriate vaccination regimen and/or dosage of glycopeptides of the invention to be administered (e.g., as in a vaccine formulation), T cell (e.g., CTL or T helper) memory is evaluated. For example, at week 16, a month after the third and last vaccine immunization, the generation of T cell memory can be studied; e.g., relying on the current knowledge that distinguishes T cell functional phenotypes depending upon the expression of specific chemokine/lymphokine receptors. The expression of CCR7 can be measured, CCR7 is the same chemokine receptor expressed on mature DC, controls T cells homing to lymphoid organs and divides memory T cells into two functionally distinct subsets:
 i. CCR7+CD45RA-IL15r+ is the phenotype that distinguishes central memory T cells ($T^{cm}$).
 ii. CCR7-CD45RA-IL15r+ is the phenotype that distinguishes effector memory T cells ($T^{em}$).

The size of the expansion of effector memory T cells, e.g., Tn-specific T cells, generated in vivo by glycopeptide vaccinations of the invention can be determined. For example, FACS analysis with individual glycopeptides/A2 tetramers can be performed, e.g., co-staining with the markers: 1) CCR7 by using a CCL21-Ig fusion protein; and 2) anti-IL15r monoclonal antibodies (e.g., from Pharmingen, San Diego, Calif.).

To identify circulating Tn-specific CCR7-IL15r+$T^{em}$ FACS analysis in combination with A2/glycopeptides tetramers can be used. As a functional control, the same CCR7-IL15r+ CD8+ cell preparation can be studied for IFN-γ production in response to individual glycopeptides. To confirm and support the results ex vivo, CCR7-, IL15r+ CD8+ cells can be stimulated in vitro and cultured for a week with the immunizing glycopeptide pool. CTL activity in response to individual glycopeptides and to Tn-expressing A2+ tumors can be measured by $^{51}$Cr release assay.

Vaccine administration, experimental design, management of toxicity and criteria for premature termination: Glycopeptides of the invention can be synthesized by any well-established method; e.g., Tn-containing glycopeptides of the length of 9 amino acids can be synthesized as described herein. Mass spectrometry analysis can be performed to assess, and insure, glycopeptide purity; e.g., in one embodiment a glycopeptide purity of ≥97% is desired. Glycopeptides of the invention can be pooled for vaccine formulation. Glycopeptides of the invention can be administered in any regimen or format, e.g., by inhalation or subcutaneously (s.c.); wherein one embodiment an s.c. formulation comprises glycopeptides of the invention emulsified with adjuvant, e.g., emulsified in incomplete Freund's adjuvant (IFA) (Life Technologies) at the dose of 0.5 mgm/glycopeptide (pool=1.5 mg). Patients can receive one or multiple administrations, e.g., three (3) vaccine injections 4 weeks apart.

In one embodiment, to measure the primary Tn-specific CTL expansion, e.g., after one (1) or more vaccine dose(s) (administrations), a blood sample (e.g., about 50 ml) is collected, e.g., at week 4 prior to the second vaccination.

To measure CTL or T helper memory, a third blood sample (50 ml) can be collected, e.g., at week 16, a month after the third and last vaccine boost. PSA levels can be monitored from the same blood samples. Safety can be assessed by changes from baseline in the following parameters: physical and ophthalmologic examinations findings, vital sign measurements, clinical laboratory test results, and performance scores. The incidence, severity and causal relationship of adverse events to the study drug can be evaluated. Serious adverse events, study discontinuations due to study drug, and deaths can be summarized.

In one embodiment, a low dosage (e.g., 0.1, 0.2, 0.3, 0.4 or 0.5 mg each/injection) and short length (5, 6, 7, 8, 9, 10, 11, 12, 13, 14 or more amino acids) suggest that glycopeptides will be no different than peptides administered in incomplete adjuvant (e.g., IFA).

Potency assays with glycopeptides in vivo in C57BL/6 mice and MUC1/MT double transgenic mice as well as in vitro studies in normal A2 donors showed efficacy in generating Tn-specific cytotoxic T cell responses in the absence of T cell help and immunological adjuvant by using very low glycopeptide doses (nM range).

Clinical efforts have validated the safety of peptides in incomplete adjuvant; examples of published relevant clinical trials that tested peptides in incomplete adjuvant in a variety of tumors are:
1. Powell (1997) Phenotypic and functional maturation of tumor antigen-reactive CD8+ T lymphocytes in patients undergoing multiple course peptide vaccination. J. Immuother. 27:36.
2. Peter (2001) Induction of a cytotoxic T-cell response to HIV-1 proteins with short synthetic peptides and human compatible adjuvants. Vaccine 19:4121.
3. Schaed (2002) T-cell responses against tyrosinase 368-376 (370D) peptide in HLA*A0201+ melanoma patients: randomized trial comparing incomplete Freund's adjuvant, granulocyte macrophage colony-stimulating factor, and QS-21 as immunological adjuvants. Clin Cancer Res. 8:967.
4. Alexander (2002) A decaepitope polypeptide primes for multiple CD8+IFN-gamma and Th lymphocyte responses: evaluation of multiepitope polypeptides as a mode for vaccine delivery. J. Immunol. 168:6189.
5. Bettinotti (2003) Clinical and immunological evaluation of patients with metastatic melanoma undergoing immunization with the HLA-Cw*0702-associated epitope MAGE-A12:170-178. Int J Cancer. 105:210.
6. Valmori (2003) Simultaneous CD8+ T cell responses to multiple tumor antigen epitopes in a multipeptide melanoma vaccine. Cancer Immun. 2003 Oct. 28; 3:15
7. Speiser (2005) Rapid and strong human CD8+ T cell responses to vaccination with peptide, IFA, and CpG oligodeoxynucleotide 7909. J. Clin. Invest. 115:739.

Tn (α-GalNAc) has been tested in primates and in clinical trials for the generation of specific antibodies responses. Tn has been administered in a variety of different formulations, and has been always found safe and well tolerated. Examples of different formulations of Tn-containing glycoconjugates for antibodies responses in cancer immunotherapy, including clinical trials and efficiency in primates, include:
1. Slovin (2003) Fully synthetic carbohydrate-based vaccines in biochemically re-lapsed prostate cancer: clinical trial results with alpha-N-acetylgalactosamine-O-serine/threonine conjugate vaccine. J. Clin. Oncol. 21:4292.
2. Slovin (2005) Thomsen-Friedenreich (TF) antigen as a target for prostate cancer vaccine: clinical trial results with TF cluster (c)-KLH plus QS21 conjugate vaccine in patients with biochemically relapsed prostate cancer. Cancer Immunol Immunother. 54:694.
3. Lo-Man (2004) A fully synthetic therapeutic vaccine candidate targeting carcinoma-associated Tn carbohydrate antigen induces tumor-specific antibodies in nonhuman primates. Cancer Research. 64:4987.
4. Grigalevicius (2005) Chemoselective assembly and immunological evaluation of multiepitopic glycoconjugates bearing clustered Tn antigen as synthetic anticancer vaccines. Bioconj. Chem. 16:1149.
5. Freire (2006) Enzymatic large-scale synthesis of MUC6-Tn glycoconjugates for antitumor vaccination. Glycobiology. 16:390.

In one embodiment, administration of glycopeptides of the invention also results in the expansion of antigen specific, e.g., Tn-specific, antibodies (natural Tn-specific antibodies are always present in patients with carcinomas). In one embodiment, B cell stimulation by glycopeptides of the invention is advantageous; B cell stimulation will not jeopardize the success of a CTL- or T helper-based immunotherapy, but on the contrary may represent a great advantage to insure success. For example, in one aspect, anti-tumor antigen antibodies generated (elicited) by vaccines of this invention induce anti-tumor antigen antibodies, e.g., anti-Tn antibodies, and these antibodies in turn induce antibody-mediated cytotoxicity (ADCC) of tumor cells. This ADCC effect can be an addition to (augment) a CTL-mediated tumor lysis. In one embodiment, anti-tumor antigen specific B cells, e.g., Tn-specific B cells, are very efficient antigen presenting cells (APCs) for CD8+ cytotoxic T cell or T helper cell priming, thus increasing (augmenting) the success of the vaccines and methods (e.g., vaccination protocols) of this invention.

A number of aspects of the invention have been described. Nevertheless, it will be understood that various modifications may be made without departing from the spirit and scope of the invention. Accordingly, other aspects are within the scope of the following claims.

---

What is claimed is:

1. An isolated or synthetic glycopeptide or glycoconjugate consisting of:
at least one carbohydrate moiety conjugated or linked to a peptide consisting of:

```
FLFPDTRAV,      (SEQ ID NO: 2)
or

FLFPDTRYV;      (SEQ ID NO: 3)
or

FLPDTRFYV;      (SEQ ID NO: 1)
``` wherein the at least one carbohydrate moiety is a α-Gal-[1->3]-β-GalNAc or a N-Acetylgalactosamine (GalNAc, 2-Acetamido-2-deoxy-D-galactopyranose or N-Acetyl -D-galactosamine).

2. A composition comprising one or more glycopeptides or glycoconjugates of claim 1.

3. A pharmaceutical composition or formulation comprising:
(a) one or more glycopeptides or glycoconjugates of claim 1 and a pharmaceutically acceptable excipient; or
(b) the pharmaceutical composition of (a), wherein the pharmaceutical composition is formulated for administration via a parenteral route comprising or consisting of a subcutaneous, an intravenous (IV), an intradermal, an intramuscular, an intraperitoneal, an intranasal, a transdermal or a buccal route.

4. A liposome comprising one or more glycopeptides or glycoconjugates of claim 1.

5. A nanoparticle comprising one or more glycopeptides or glycoconjugates of claim 1.

6. A cancer vaccine comprising: one or more glycopeptides or glycoconjugates of claim 1.

7. The glycopeptide or glycoconjugate of claim 1, further comprising a second carbohydrate moiety,
wherein the first carbohydrate moiety consists of a α-Gal-[1->3]-β-GalNAc or a N-Acetylgalactosamine,
and a second carbohydrate moiety comprises or consists of a β-D-glucose, a β-D-galactose, a β-D-mannose, an α-L-Fucose, an N-Acetylglucosamine (N-Acetyl-D-Glucosamine, or GlcNAc, or NAG), an aminoglycoside or amino hexose sugar, an N-Acetylneuraminic acid (Neu5Ac or NANA), a sialic acid, a Neuraminic acid (5-amino-3,5-dideoxy-D-glycero-D-galacto-non-2-ulosonic acid), a xylose or a pentose sugar.

8. The glycopeptide or glycoconjugate of claim 1, wherein the at least one carbohydrate moiety is conjugated or linked to the peptide:

(a) at an amino acid residue central to the peptide, or
(b) at an amino acid residue that is not involved in the peptide's binding to an MHC polypeptide.

9. The glycopeptide or glycoconjugate of claim 1, wherein the at least one carbohydrate moiety is conjugated or linked to the peptide:
(a) at no amino acid residue within two residues of the amino terminal end or carboxy terminal end of the peptide, or
(b) at least three amino acid residues in from either the amino terminal or carboxy terminal end of the peptide.

10. The glycopeptide or glycoconjugate of claim 1, further comprising a second carbohydrate moiety consisting of a monosaccharide, a disaccharide, a trisaccharide or a polysaccharide.

11. A glycopeptide or glycoconjugate consisting of:

```
FLPD(X-T) RFYV (FLPDTRFYV is SEQ ID NO: 1),

FLFPD(X-T) RAV (FLFPDTRAV is SEQ ID NO: 2),
or

FLFPD(X-T) RYV (FLFPDTRYV is SEQ ID NO: 3),
``` wherein X consists of an β-Gal-[1->3]-β-GalNAc or a N-Acetylgalactosamine.

12. The glycopeptide or glycoconjugate of claim 1, wherein the peptide, or at least one amino acid in the peptide, comprises or consists of a peptidomimetic.

13. The glycopeptide or glycoconjugate of claim 1, wherein the peptide comprises or consists of an isolated, synthetic or recombinantly generated peptide or amino acid.

14. The glycopeptide or glycoconjugate of claim 10, wherein the second carbohydrate moiety is mono- or poly-sialylated, or not sialated.

15. A The vaccine comprising a peptide that:
(a) comprises an FLFPDTRAV (SEQ ID NO:2), FLFPDTRYV (SEQ ID NO:3) or FLPDTRFYV (SEQ ID NO:1); or
(b) consists of a mixture of an FLFPDTRAV (SEQ ID NO:2), FLFPDTRYV (SEQ ID NO:3) or FLPDTRFYV (SEQ ID NO:1).

16. The vaccine of claim 15, further comprising an adjuvant.

17. The vaccine of claim 15, further comprising a non-specific immuno-stimulator, or a granulocyte-macrophage colony-stimulating factor polypeptide; or a sargramostim.

18. The vaccine of claim 15, wherein the vaccine is formulated for administration parentally or orally, or systemically or topically, or the vaccine is formulated for administration via a parenteral route or via a route comprising a subcutaneous, an intramuscular, an intravenous (IV), an intradermal, an intramuscular, an intraperitoneal, an intranasal, an intradermal, a transdermal or a buccal route, or the vaccine is formulated for administration parenterally by bolus injection or by gradual perfusion over time, or the vaccine is formulated for administration by an oral or a topical route.

19. A liposome comprising the vaccine of claim 15.

20. The vaccine of claim 15, formulated as: a sterile solution for injection; a powder; a lyophilized or a freeze-dried composition; a liquid; an emulsion; a lyophilized powder; a spray; a cream; a lotion; a controlled release formulation; a tablet; a pill; a gel; a patch; in an implant or in a spray; an aqueous or a non-aqueous isotonic sterile injection solution; or an aqueous or a non-aqueous sterile suspension.

21. The glycopeptide or glycoconjugate of claim 10, wherein the second carbohydrate moiety consists of at least one tumor-associated carbohydrate antigen (TACA), or at least one tumor-derived carbohydrate.

22. The vaccine of claim 16, wherein the adjuvant comprises: an incomplete Freund's adjuvant (IFA); an alum; an aluminum phosphate; an aluminum hydroxide; a squalene; a complete Freund's adjuvant (CFA), a levamisole; a muramyl dipeptide (MDP); a monophosphoryl lipid (MPL); a monophosphoryl lipid A (MPLA); a glycosylceramide, a triacyl lipid A; an oil in water emulsion comprising a monophosphoryl lipid A; a threonyl-MDP in an oil-in-water (o/w) emulsion vehicle; a pluronic L121 or a poloxamer 401; a mucosal adjuvant comprising a detoxified mutant A subunit of a cholera toxin (CT); an E. coli heat labile toxin (LT1 or LT2); or, any combination thereof.

23. The isolated or synthetic glycopeptide or glycoconjugate of claim 1, wherein the peptide conjugated or linked to the at least one carbohydrate moiety consists of FLFPDTRAV (SEQ ID NO:2).

24. The isolated or synthetic glycopeptide or glycoconjugate of claim 1, wherein the peptide conjugated or linked to the at least one carbohydrate moiety consists of: FLFPDTRYV (SEQ ID NO:3).

25. The isolated or synthetic glycopeptide or glycoconjugate of claim 1, wherein the peptide conjugated or linked to the at least one carbohydrate moiety consists of: FLPDTRFYV (SEQ ID NO:1).

26. The isolated or synthetic glycopeptide or glycoconjugate of claim 1, wherein the at least one carbohydrate moiety is a α-Gal-[1->3]β-GalNAc.

27. The isolated or synthetic glycopeptide or glycoconjugate of claim 1, wherein the at least one carbohydrate moiety is an N-Acetylgalactosamine (GalNAc, 2-Acetamido-2-deoxy-D-galactopyranose or N-Acetyl-D-galactosamine).

28. The glycopeptide or glycoconjugate of claim 11, wherein the glycopeptide or glycoconjugate consists of FLPD(X-T) RFYV and wherein X consists of an α-Gal-[1->3]-β-GalNAc or a N-Acetylgalactosamine.

29. The glycopeptide or glycoconjugate of claim 11, wherein the glycopeptide or glycoconjugate consists of FLFPD(X-T)RAV and wherein X consists of an β-Gal-[1->3]-β-GalNAc or a N-Acetylgalactosamine.

30. The glycopeptide or glycoconjugate of claim 11, wherein the glycopeptide or glycoconjugate consists of FLFPD(X-T)RYV, and wherein X consists of an α-Gal-[1->3]-β-GalNAc or a N-Acetylgalactosamine.

31. The glycopeptide or glycoconjugate of claim 11, further comprising a second carbohydrate moiety consisting of a monosaccharide, a disaccharide, a trisaccharide or a polysaccharide.

* * * * *